(12) United States Patent
Doi

(10) Patent No.: US 8,496,575 B2
(45) Date of Patent: Jul. 30, 2013

(54) MEASURING ENDOSCOPE APPARATUS, PROGRAM AND RECORDING MEDIUM

(75) Inventor: Takahiro Doi, Tokyo (JP)

(73) Assignee: Olympus Corporation, Tokyo (JP)

( * ) Notice: Subject to any disclaimer, the term of this patent is extended or adjusted under 35 U.S.C. 154(b) by 1306 days.

(21) Appl. No.: 11/939,115

(22) Filed: Nov. 13, 2007

(65) Prior Publication Data

US 2009/0043161 A1    Feb. 12, 2009

(30) Foreign Application Priority Data

Nov. 14, 2006  (JP) ............................... P2006-307639
Jun. 4, 2007   (JP) ............................... P2007-147947

(51) Int. Cl.
| | |
|---|---|
| A61B 1/04 | (2006.01) |
| A61B 1/00 | (2006.01) |
| A61B 8/00 | (2006.01) |
| G06T 15/00 | (2011.01) |
| G06T 15/10 | (2011.01) |
| G06T 15/20 | (2011.01) |

(52) U.S. Cl.
USPC ........... 600/117; 600/443; 600/109; 345/419; 345/427

(58) Field of Classification Search
USPC ................. 600/117, 160, 111, 146, 118, 425, 600/114, 139; 348/65, 46; 356/602, 603; 606/33; 345/634, 427
See application file for complete search history.

(56) References Cited

U.S. PATENT DOCUMENTS

| | | | |
|---|---|---|---|
| 4,385,317 A | 5/1983 | Furuya et al. | |
| 5,669,871 A * | 9/1997 | Sakiyama | ...................... 600/117 |
| 6,069,713 A * | 5/2000 | Kusama | ........................ 358/452 |
| 6,573,499 B1 | 6/2003 | Sasajima et al. | |
| 6,765,204 B2 | 7/2004 | Mizuno et al. | |
| 6,914,623 B2 | 7/2005 | Ogawa | |
| 6,936,819 B2 | 8/2005 | Sasajima et al. | |

(Continued)

FOREIGN PATENT DOCUMENTS

| | | |
|---|---|---|
| JP | 55-128241 A | 10/1980 |
| JP | 02-244021 A | 9/1990 |

(Continued)

OTHER PUBLICATIONS

Japanese Office Action dated Jan. 4, 2012 (and English translation thereof) in counterpart Japanese Application No. 2006-307639.

(Continued)

Primary Examiner — John P Leubecker
Assistant Examiner — Ronald D Colque
(74) Attorney, Agent, or Firm — Holtz, Holtz, Goodman & Chick, PC

(57) ABSTRACT

The present invention provides a measuring endoscope apparatus which includes an endoscope that photoelectrically converts an image of an object to generate an imaging signal, a signal processing section that processes the imaging signal to generate image data, a distance measuring section that calculates an object distance based on a principle of triangulation using the image data, and a display section that displays the image of the object based on the image data. The measuring endoscope apparatus further includes a measuring section that calculates a size of the mark indicating a size of the object based on the object distance and a view angle of the endoscope. The display section also displays a mark along with the image of the object based on the image data.

16 Claims, 30 Drawing Sheets

U.S. PATENT DOCUMENTS

| | | | |
|---|---|---|---|
| 7,217,923 B2 | 5/2007 | Sasajima et al. | |
| 7,435,959 B2 | 10/2008 | Sasajima et al. | |
| 7,791,021 B2 | 9/2010 | Sasajima et al. | |
| 8,304,724 B2 | 11/2012 | Sasajima et al. | |
| 2004/0145722 A1* | 7/2004 | Uomori et al. | 356/4.01 |
| 2004/0225185 A1* | 11/2004 | Obata et al. | 600/118 |
| 2004/0258328 A1* | 12/2004 | Adler | 382/286 |
| 2005/0135192 A1* | 6/2005 | Fairbairn | 367/111 |
| 2006/0050383 A1* | 3/2006 | Takemoto et al. | 359/462 |
| 2007/0002015 A1* | 1/2007 | Mohri et al. | 345/157 |
| 2010/0208046 A1* | 8/2010 | Takahashi | 348/65 |

FOREIGN PATENT DOCUMENTS

| | | |
|---|---|---|
| JP | 10-323322 A | 12/1998 |
| JP | 2001-110862 A | 4/2001 |
| JP | 2001-167272 A | 6/2001 |
| JP | 2001-209827 A | 8/2001 |
| JP | 2001-269306 A | 10/2001 |
| JP | 2002-156212 A | 5/2002 |
| JP | 2002-159021 A | 5/2002 |
| JP | 2002-345735 A | 12/2002 |
| JP | 2004-004118 A | 1/2004 |
| JP | 2004-121546 A | 4/2004 |
| JP | 2006-136706 A | 6/2006 |
| JP | 2006-230906 A | 9/2006 |

OTHER PUBLICATIONS

Japanese Office Action dated Sep. 18, 2012 (and English translation thereof) in counterpart Japanese Application No. 2008-145791.

* cited by examiner

*FIG. 15*

| X | θ | Y |
|---|---|---|
| 1mm | 10° | Y11 |
| 1mm | 20° | Y12 |
| ⋮ | ⋮ | ⋮ |
| 1mm | 45° | Y1n |
| 2mm | 10° | Y21 |
| 2mm | 20° | Y22 |
| ⋮ | ⋮ | ⋮ |
| 2mm | 45° | Y2n |
| ⋮ | ⋮ | ⋮ |

| X | Y | θ |
|---|---|---|
| 1mm | 1mm | θ 11 |
| 1mm | 2mm | θ 12 |
| ⋮ | ⋮ | ⋮ |
| 1mm | 5mm | θ 15 |
| 2mm | 1mm | θ 21 |
| 2mm | 2mm | θ 22 |
| ⋮ | ⋮ | ⋮ |
| 2mm | 5mm | θ 25 |
| ⋮ | ⋮ | ⋮ |

MEASURING ENDOSCOPE APPARATUS, PROGRAM AND RECORDING MEDIUM

CROSS-REFERENCE TO RELATED APPLICATIONS

This application claims the priorities of Japanese Patent Application No. 2006-307639 filed on Nov. 14, 2006, and Japanese Patent Application No. 2007-147947 filed on Jun. 4, 2007, the contents of both of which are incorporated herein by reference.

BACKGROUND OF THE INVENTION

1. Field of the Invention

The present invention relates to a measuring endoscope apparatus which has a function of calculating spatial coordinates of a point on an object and a distance to an image forming surface of an endoscope from the point on the object based on the principle of triangulation using image data, and a program for controlling the operation of the measuring endoscope apparatus. The present invention also relates to a recording medium recording the program.

2. Description of the Related Art

Industrial endoscopes are used to observe or examine internal flaws, corrosion, etc. of a boiler, turbine, engine, chemical plant, water pipe and the like. To ensure observation and examination of a variety of objects, an industrial endoscope is provided with plural types of optical adapters and has a replaceable distal end portion.

A stereo optical adapter which forms right and left fields of view on an observation optical system is one of the optical adapters. Japanese Patent Application, First Publication No. 2006-136706 describes a measuring endoscope apparatus which uses a stereo optical adapter to acquire three-dimensional spatial coordinates of the object using the principle of triangulation based on the coordinates of right and left object distance measuring points of optical systems when the image of the object is captured by the right and left optical systems, and provides a user in real time with an object distance from a picked-up live image.

SUMMARY OF THE INVENTION

The present invention provides a measuring endoscope apparatus which includes an endoscope that photoelectrically converts an image of an object to generate an imaging signal, signal processing section that processes the imaging signal to generate image data, distance measuring section that calculates an object distance based on a principle of triangulation using the image data, and display section that displays the image of the object based on the image data, and further includes measuring section that calculates a size of the mark indicating a size of the object based on the object distance and a view angle of the endoscope. The display section also displays a mark along with the image of the object based on the image data.

In the measuring endoscope apparatus, the measuring section calculates a size of the mark on the object at a position apart by the object distance based on the object distance, the view angle of the endoscope and a display size of the mark.

In the measuring endoscope apparatus, the measuring section calculates a display size of the mark based on the object distance, the view angle of the endoscope and a size of the mark on the object at a position apart by the object distance.

In the measuring endoscope apparatus, the display section displays the image of the object and displays the mark overlying an aim indicating an object distance measuring point of the object distance.

In the measuring endoscope apparatus, the display section displays the image of the object and the mark and displays a value of a size of the mark on the object.

In the measuring endoscope apparatus, the display section displays the image of the object and displays the mark around a frame of the image of the object at a position apart by the object distance.

In the measuring endoscope apparatus, the display section displays the image of the object and the mark and displays the object distance.

In the measuring endoscope apparatus, the measuring section calculates the size of the mark based on a predetermined operational expression.

In the measuring endoscope apparatus, the measuring section calculates the size of the mark based on a value in a predetermined table.

The present invention also provides a program for controlling an operation of a measuring endoscope apparatus having an endoscope that photoelectrically converts an image of an object to generate an imaging signal, signal processing section that processes the imaging signal to generate image data, distance measuring section that calculates an object distance based on a principle of triangulation using the image data, and display section that displays the image of the object based on the image data, the program allowing the measuring endoscope apparatus to execute a measuring process of calculating a size of the mark indicating a size of the object based on the object distance and a view angle of the endoscope and a display process of displaying the mark along with the image of the object based on the image data.

In the program, the measuring process calculates a size of the mark on the object at a position apart by the object distance based on the object distance, the view angle of the endoscope and a display size of the mark.

In the program, the measuring process calculates a display size of the mark based on the object distance, the view angle of the endoscope and a size of the mark on the object at a position apart by the object distance.

In the program, the display process displays the image of the object and displays the mark overlying an aim indicating an object distance measuring point of the object distance.

In the program, the display process displays the image of the object and the mark and displays a value of a size of the mark on the object at a position apart by the object distance.

In the program, the display process displays the image of the object and displays the mark around a frame of the image of the object.

In the program, the display process displays the image of the object and the mark and displays the object distance.

In the program, the measuring process calculates the size of the mark based on a predetermined operational expression.

In the program, the measuring process calculates the size of the mark based on a value in a predetermined table.

The present invention further provides a computer-readable recording medium recording the foregoing program.

The present invention provides a measuring endoscope apparatus which includes an endoscope that photoelectrically converts an image of an object to generate an imaging signal, signal processing section that processes the imaging signal to generate image data, distance measuring section that calculates coordinates of a point on the object and an object distance to an image forming surface of the endoscope from the point on the object based on a principle of triangulation using the image data, and display section that displays the image of the object based on the image data, and further includes mark display section that executes a process of displaying a first mark indicating an inclination of the object in a depthwise direction of the image based on the object distances for a plurality of points on the object.

The measuring endoscope apparatus further includes measuring section that calculates distances among the plurality of points on the object based on spatial coordinates of the plurality of points, and the mark display section further executes a process of displaying a second mark indicating the size of the object and a distance between two points on the object based on positions of a plurality of points on an image forming surface corresponding to the plurality of points on the object, and a distance between two points on the object.

The measuring endoscope apparatus further includes measuring section that calculates distances among the plurality of points on the object based on spatial coordinates of the plurality of points, and the mark display section further executes a process of displaying a second mark indicating the size of the object and a distance between two points on the object based on a preset numerical value indicating a distance on the object and the distances among the plurality of points on the object calculated by the measuring section.

In the measuring endoscope apparatus, the mark display section further executes a process of displaying values of the distances among the plurality of points on the object.

In the measuring endoscope apparatus, the mark display section further executes a process of displaying values of the distances among the plurality of points on the object over the image of the object.

In the measuring endoscope apparatus, the mark display section further executes a process of displaying values of the distances among the plurality of points on the object at a location other than where the image of the object is displayed.

In the measuring endoscope apparatus, the mark display section further executes a process of displaying values of the distances among the plurality of points on the object in a vicinity of the second mark.

In the measuring endoscope apparatus, the first mark and the second mark may be identical.

The present invention provides a program which controls the operation of a measuring endoscope apparatus which includes an endoscope that photoelectrically converts an image of an object to generate an imaging signal, signal processing section that processes the imaging signal to generate image data, distance measuring section that calculates coordinates of a point on the object and an object distance to an image forming surface of the endoscope from the point on the object based on a principle of triangulation using the image data, and display section that displays the image of the object based on the image data, and allows the measuring endoscope apparatus to execute a mark display process of executing a process of displaying a first mark indicating an inclination of the object in a depthwise direction of the image based on object distances for a plurality of points on the object.

BRIEF DESCRIPTION OF THE DRAWINGS

FIG. 15 is a reference diagram showing the contents of a table used in the object measuring process (first operation example) according to one embodiment of the present invention.

DETAILED DESCRIPTION OF THE PREFERRED EMBODIMENT

Figure 1:
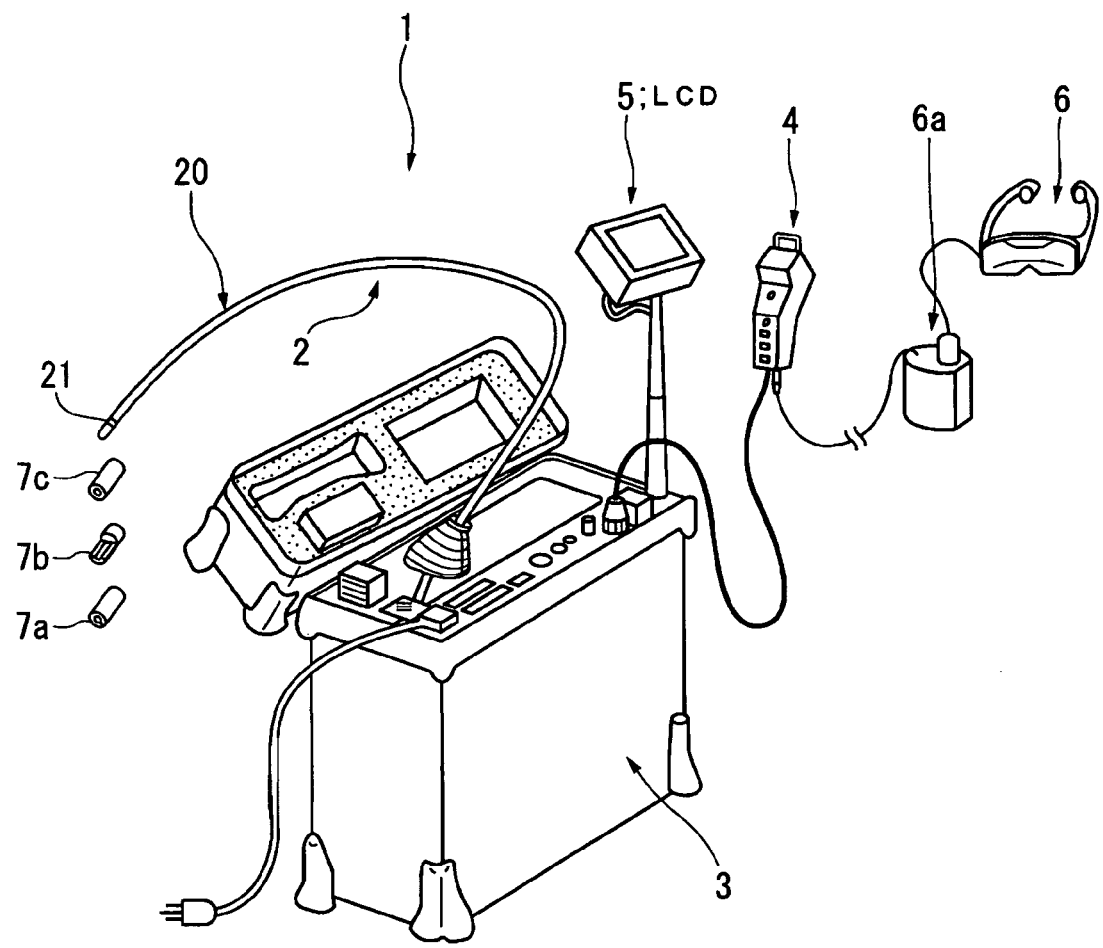
FIG. 1 is a perspective view showing the general configuration of a measuring endoscope apparatus according to one embodiment of the present invention.

Preferred embodiments of the present invention will be described below referring to the accompanying drawings. FIG. 1 shows the general configuration of an endoscope apparatus (measuring endoscope apparatus) according to one embodiment of the present invention. As shown in FIG. 1, an endoscope apparatus 1 mainly comprises an endoscope 2 having a thin elongated insertion part 20, a main unit 3 or a control device which has a housing section for housing the insertion part 20 of the endoscope 2, a remote controller 4 for performing necessary operations at the time of executing various operational controls of the entire apparatus, an LCD (liquid crystal monitor) 5 or a display device which displays an endoscope image, the content of an operational control (e.g., process menu), etc., an FMD (Face Mount Display) 6 which ensures three-dimensional imaging of a normal endoscope image or a virtual stereo image thereof, and an FMD adapter 6a which supplies image data to the FMD 6.

The insertion part 20 is configured by serially providing a hard distal end portion 21, a flexible pipe portion having flexibility, and a bending portion 22 (see FIG. 2) which is bendable, for example, up and down and right and left. Various optical adapters, such as stereo optical adapters 7a, 7b having two observation areas or a normal observation optical adapter 7c having a single observation area, are mountable to the distal end portion 21.

Figure 2:
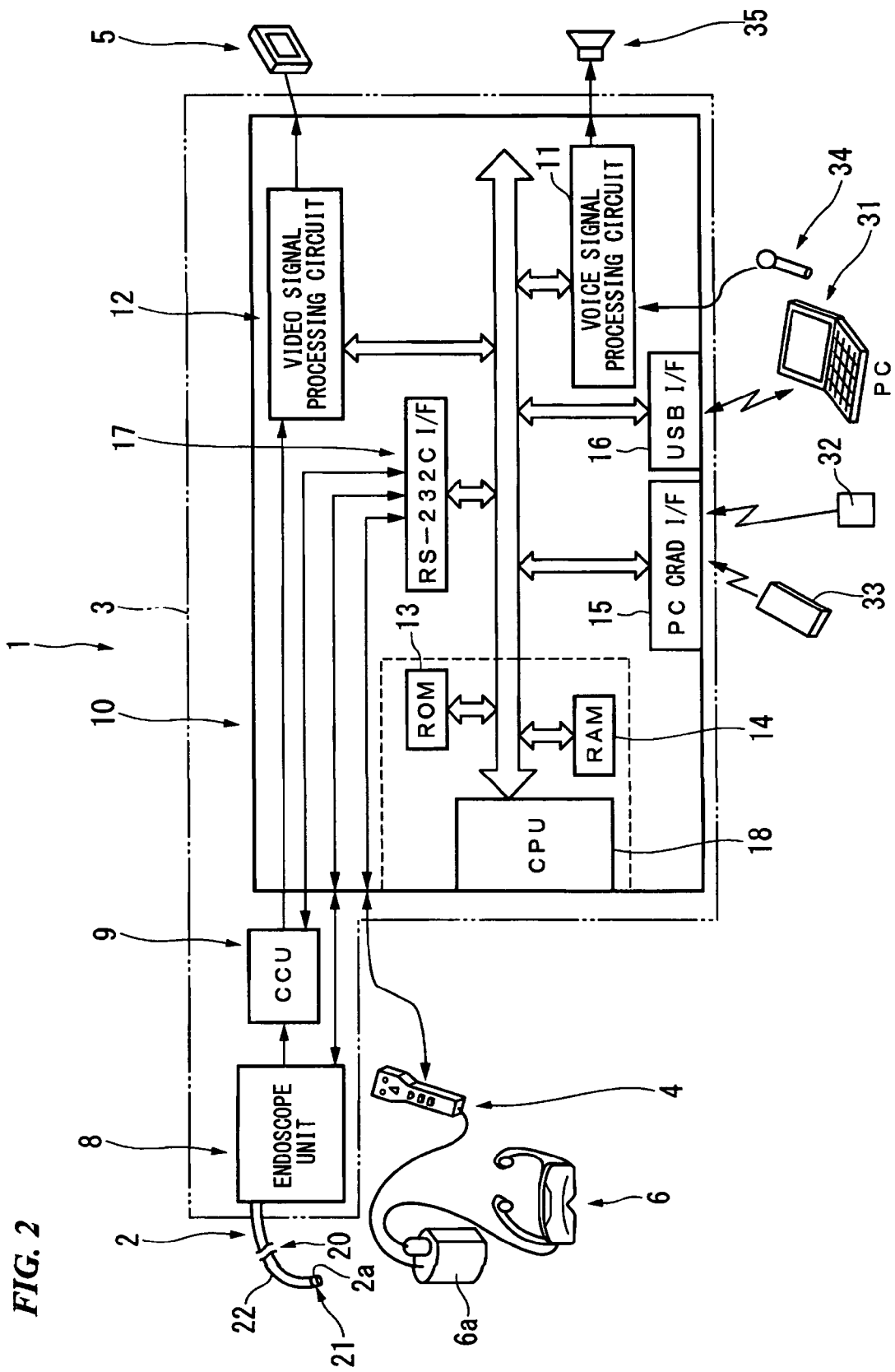
FIG. 2 is a block diagram showing the internal configuration of the measuring endoscope apparatus according to one embodiment of the present invention.

As shown in FIG. 2, an endoscope unit 8, a CCU (camera control unit) 9 and a control unit 10 are provided in the main unit 3, and the proximal end portion of the insertion part 20 is connected to the endoscope unit 8. The endoscope unit 8 comprises a light source unit (not shown) which supplies necessary illumination light at the time of observation and a bending unit (not shown) which bends the bending portion 22 constituting the insertion part 20.

A solid state imaging device 2a is incorporated in the distal end portion 21 of the insertion part 20. The solid state imaging device 2a photoelectrically converts an object image formed through the optical adapter to generate an imaging signal. The imaging signal output from the solid state imaging device 2a is input to the CCU 9. The imaging signal is converted to a video signal (image data), e.g, a NTSC signal, in the CCU 9 before being supplied to the control unit 10.

Provided in the control unit 10 are a voice signal processing circuit 11, a video signal processing circuit 12 to which a video signal is input, a ROM 13, a RAM 14, a PC card I/F (interface) 15, a USB I/F (interface) 16, an RS-232C I/F (interface) 17, etc., and a CPU 18 which executes various functions thereof based on a main program to perform an operational control.

The RS-232C I/F 17 is connected with the CCU 9 and the endoscope unit 8 as well as the remote controller 4 which executes control and operational instructions of the CCU 9, the endoscope unit 8 and the like. As a user manipulates the remote controller 4, communications necessary to control the operations of the CCU 9 and the endoscope unit 8 are carried out based on the contents of the manipulation.

The USB I/F 16 is an interface to electrically connect the main unit 3 to a personal computer 31. As the main unit 3 is connected to the personal computer 31 via the USB I/F 16, it is possible to execute an instruction to display an endoscope image and various instruction controls, such as image processing at the time of measurement, on the personal computer 31, and input and output control information, data or the like necessary in various processes between the main unit 3 and the personal computer 31.

A recording medium or a so-called memory card, such as a PCMCIA memory card 32 or flash memory card 33, is freely mounted to or dismounted from the PC card I/F 15. Mounting the memory card to the PC card I/F 15 can ensure the retrieval of data, such as control process information and image information, stored in the memory card to the main unit 3, or recording of data, such as control process information and image information, into the memory card under the control of the CPU 18.

The video signal processing circuit 12 performs a process of combining an operation-menu based display signal generated under the control of the CPU 18 a process necessary to display a video signal on the screen of the LCD 5, or the like for the purpose of displaying a synthesized image of an endoscope image supplied from the CCU 9 and a graphics-based operation menu, and supplies the video signal to the LCD 5. The video signal processing circuit 12 can merely perform a process of displaying an endoscope image or an image of an operation menu or the like alone. Therefore, an endoscope image, an operation menu image, a synthesized image of an endoscope image and an operation menu image or the like is displayed on the screen of the LCD 5.

The voice signal processing circuit 11 is supplied with a voice signal, which is collected and generated by a microphone 34 and is to be recorded on a recording medium like a memory card, a voice signal acquired by reproduction from a recording medium like a memory card, or a voice signal generated by the CPU 18. The voice signal processing circuit 11 performs a process, such as an amplification process, needed to reproduce the supplied voice signal, and then sends the voice signal to a speaker 35. Accordingly, a voice is output from the speaker 35.

The CPU 18 executes a program stored in the ROM 13 to control various circuit sections or the like to perform purpose-oriented processes, thereby performing the general system operation control. The RAM 14 is used by the CPU 18 as a work area for temporarily storage of data.

Figure 3:
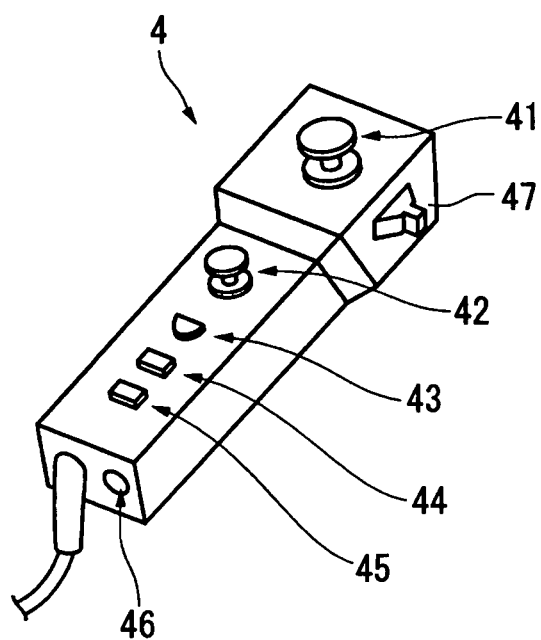
FIG. 3 is a perspective view of a remote controller of the measuring endoscope apparatus according to one embodiment of the present invention.

As shown in FIG. 3, a joystick 41, a lever switch 42, a freeze switch 43, a store switch 44 and a measurement execution switch 45 are provided on the front side of the remote controller 4. A zoom lever 47 is provided on a side face of the remote controller 4.

The joystick 41 is a switch which is operated to instruct a bending operation of the bending portion 22. As the user performs an oblique operation of the joystick 41, the bending portion 22 is bent in a direction corresponding to the tilting direction by a tilt angle. The lever switch 42 is a switch which is operated at the time of operating various kinds of graphic menus displayed or by moving a pointer when taking a measurement, and is configured approximately like the joystick 41. The freeze switch 43 is a switch associated with display on the LCD 5. The store switch 44 is a switch which is used to record a still image in a memory card when the still image is displayed by depression of the freeze switch 43. The measurement execution switch 45 is a switch to be used at the time of executing measuring software.

The freeze switch 43, store switch 44 and measurement execution switch 45 are of, for example, a depression type which gives an ON/OFF instruction by a depression operation. A connector part 46 is a connection part to which an electric cable extending from the FMD adapter 6a is connected. Connecting the electric cable to the connector part 46 can ensure stereo observation through the FMD 6. The zoom lever 47 is a switch which can be flipped frontward and rearward, and is manipulated when controlling electronic zooming. When the user flips the zoom lever 47 rearward, a telescopic (zoom-up) operation is carried out, whereas when the user flips the zoom lever 47 frontward, a wide (zoom-down) operation is carried out.

Figure 4:
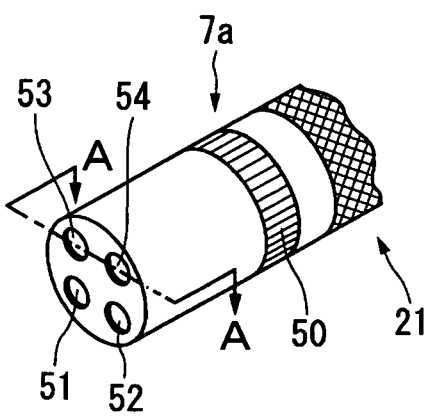
FIG. 4 is a perspective view of a stereo optical adapter used in the measuring endoscope apparatus according to one embodiment of the present invention.
Figure 5:
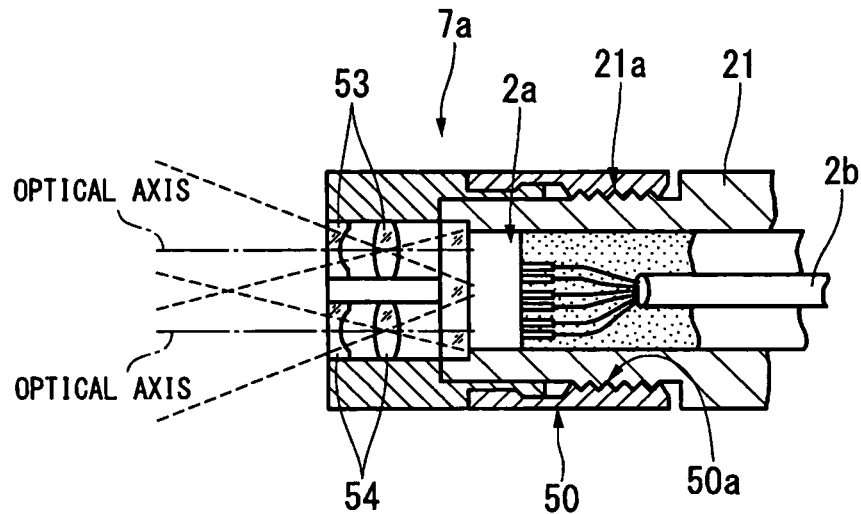
FIG. 5 is a cross-sectional view showing the internal configuration of the stereo optical adapter used in the measuring endoscope apparatus according to one embodiment of the present invention.

FIGS. 4 and 5 show the configuration of one example of the stereo optical adapter 7a which is one of optical adapters used in the endoscope apparatus 1 of the embodiment. As shown in FIGS. 4 and 5, a pair of illumination lenses 51, 52 and two objective lens systems 53, 54 are provided at the distal end face of the direct-view type stereo optical adapter 7a, and are integrally fixed by fastening a female screw 50a of a fixed ring 50 over a male screw 21a formed at the distal end portion 21 as shown in FIG. 5.

As shown in FIG. 5, two optical images are formed on the imaging surface of the solid state imaging device 2a, provided in the distal end portion 21, by the two objective lens systems 53, 54. An imaging signal photoelectrically converted by the solid state imaging device 2a is supplied to the CCU 9 to be a video signal through an electrically-connected signal line 2b and the endoscope unit 8, and is then supplied to the video signal processing circuit 12.

In the endoscope apparatus 1 of the embodiment, as shown in (a1) to (d) below, optical data of a unique optical imaging system of each endoscope 2 is measured, and is recorded in a recording medium, for example, a memory card (PCMCIA memory card 32, flash memory card 33 or the like). The optical data is as follows.

(a1) Geometric distortion correction table for two objective optical systems (a2) Geometric distortion correction table for an image transfer optical system (b) Focal distance of each of right and left image forming optical systems (c) Distance between principal points of right and left image forming optical systems (d) Optical-axis position coordinates on an image from each of right and left image forming optical systems With the personal computer 31 connected to the endoscope apparatus 1 after collection of the optical data, the following processes (1) to (5) can be executed to perform various kinds of size measurements.

(1) The optical data of (a1) to (d) is read from the memory card.

(2) A measurement object as an object is imaged by the endoscope 2 to acquire an image.

(3) The acquired image is subjected to coordinate conversion based on the optical data of (a1) to (d).

(4) Three-dimensional coordinates of an arbitrary point are acquired through matching of imaged data based on the coordinate-converted image.

(5) Various three-dimensional measurements are taken based on the three-dimensional coordinates.

Figure 6:
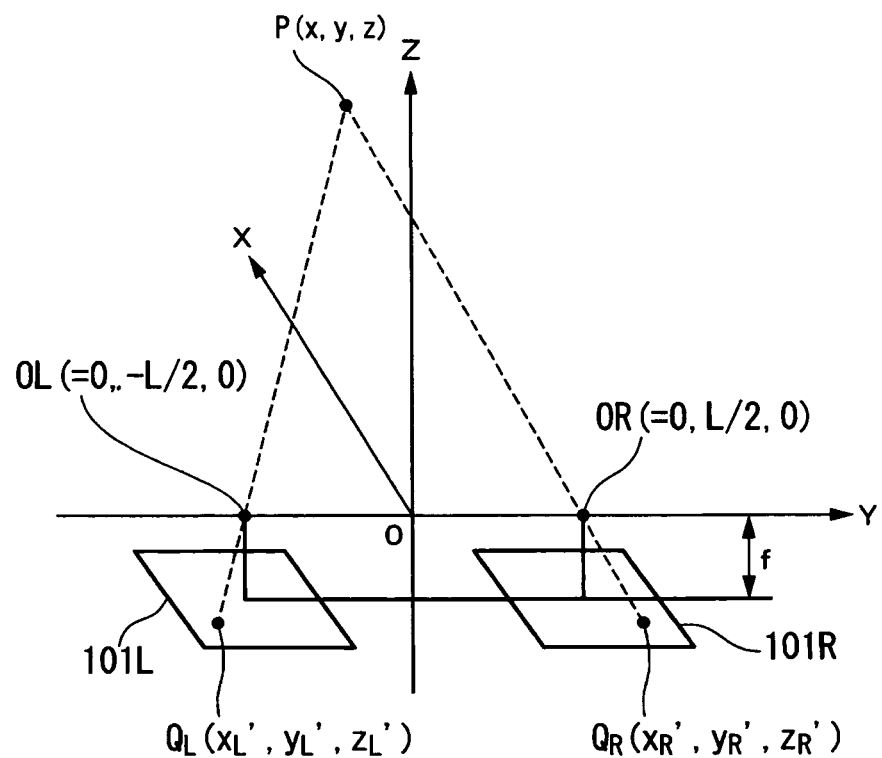
FIG. 6 is a reference diagram illustrating the principle of measuring an object distance according to one embodiment of the present invention.
Figure 7:
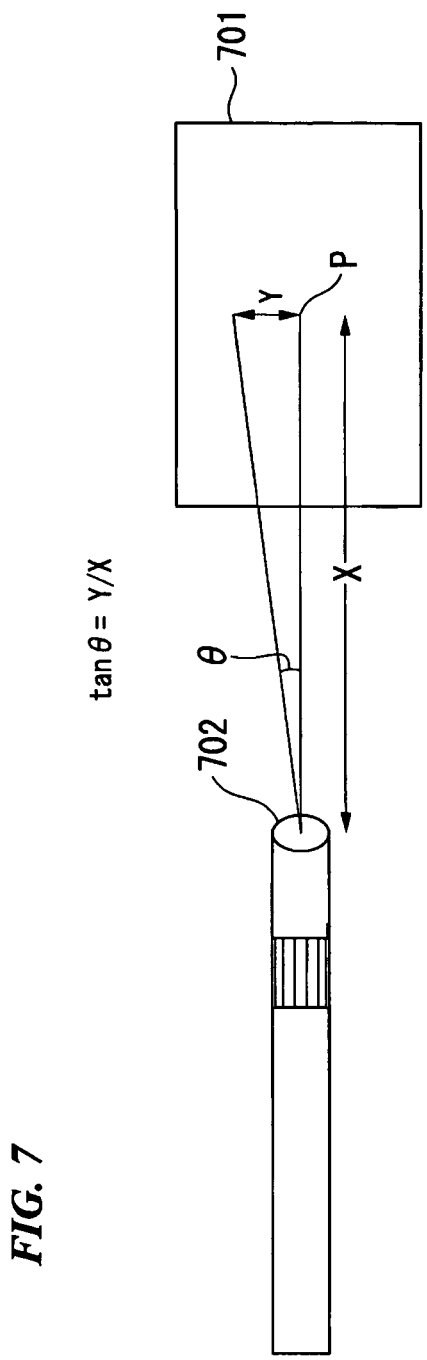
FIG. 7 is a reference diagram illustrating the principle of measuring the size of a mark according to one embodiment of the present invention.

The principle of measuring the object using the endoscope apparatus 1 of the embodiment will be explained next. FIG. 6 shows the positional relationship between a right image and a left image on the three-dimensional spatial coordinate system having x, y and z axes. FIG. 6 shows that the image of an object distance measuring point P to be measured for the distance to the object (object distance) is formed on a right image forming surface 101R and a left image forming surface 101L of the imaging device. In FIG. 6, let points OR and OL be the principle points of the optical system, let a distance f be the focal distance, let points $Q_R$ and $Q_L$ be image forming positions of the point P, and let a distance L be the distance between the point OR and the point OL.

The following equation is satisfied from a line $Q_R$-OR in FIG. 6.

$$x/xR = \{y-(L/2)\}/\{yR-(L/2)\} = z/(-f) \quad (1)$$

The following equation is satisfied from a line $Q_L$-OL.

$$x/xL = \{y+(L/2)\}/\{yL+(L/2)\} = z/(-f) \tag{2}$$

Solving the equations for x, y and z yields three-dimensional coordinates of the point P. Accordingly, the distance to the object from the distal end (the image pickup surface of the endoscope 2) of the stereo optical adapter is acquired.

The distance between the points OR and OL or the principle points of the optical system, and the focal distance of the image forming optical system are recorded as optical data beforehand. The coordinates of the point $Q_L$ are no more than the coordinates of the object distance measuring point.

The point $Q_R$ can be acquired by searching for a point corresponding to the object distance measuring point from the right image. Accordingly, when the left image is taken as a reference, for example, a corresponding point ($Q_R$) on the right image which corresponds to an object distance measuring point ($Q_L$) on the left image is searched by a matching process, and when the corresponding point on the right image is searched, the distance to the object distance measuring point can be acquired by calculating the spatial coordinates from the above equations.

An observation area 701 indicates an area which a stereo optical adapter 702 can take as an object image. A point P at the center of the observation area 701 is the object distance measuring point and its three-dimensional coordinates are acquired by solving the equations (1) and (2) for x, y and z. While a mark indicating the size of the object is displayed together with endoscope image in the embodiment, Y in the diagram shows the actual size of the mark on the object at a position apart from the stereo optical adapter 702 by an object distance X. The following equation is satisfied from a trigonometric function $\tan\theta = Y/X$.

$$Y = X \times \tan\theta \tag{3}$$

Figure 8:
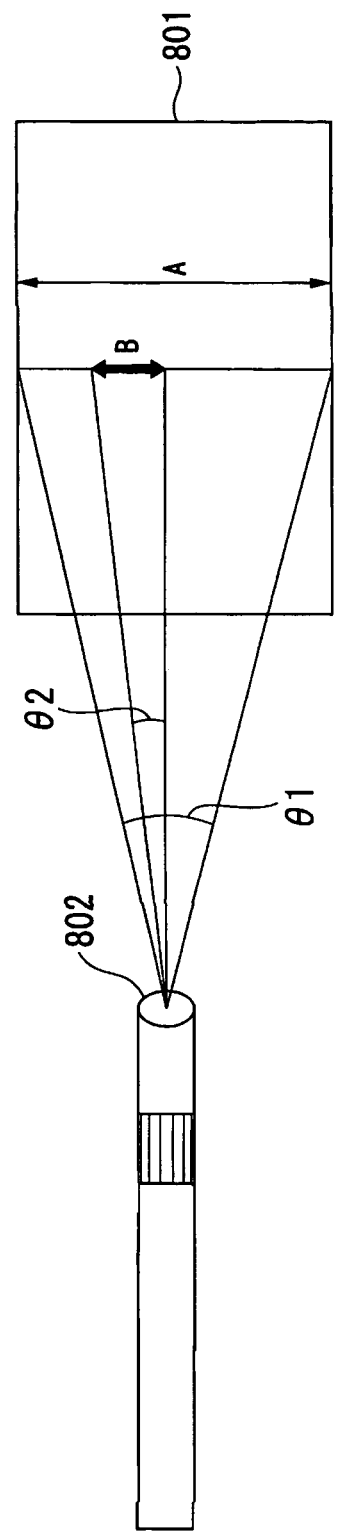
FIG. 8 is a reference diagram illustrating the principle of measuring the size of a mark according to one embodiment of the present invention.

The view angles of stereo optical adapters are fixed individually. Given that the width of an observation area 801 is A, the size of a mark is B, the view angle of a stereo optical adapter 802 is θ1 and the angle defined by the size of the mark is θ2, as shown in FIG. 8, θ1:θ2=A:B is satisfied, from which equation the following equation is derived.

$$\theta 2 = B \times \theta 1 / A \tag{4}$$

When the size of the observation area 801 is assumed to be identical to the size of an endoscope image displayed, the width A of the observation area 801 is identical to the width of the endoscope image displayed, and the size B of the mark is identical to the display size of the mark. If the value of B is predetermined, the value of θ2 can be calculated from the equation 4 since the values of A and θ1 are known previously. The value of Y can be acquired by substituting the value of θ2 acquired from the equation 4 and the value of X acquired in the aforementioned manner in the equation 3.

Figure 9:
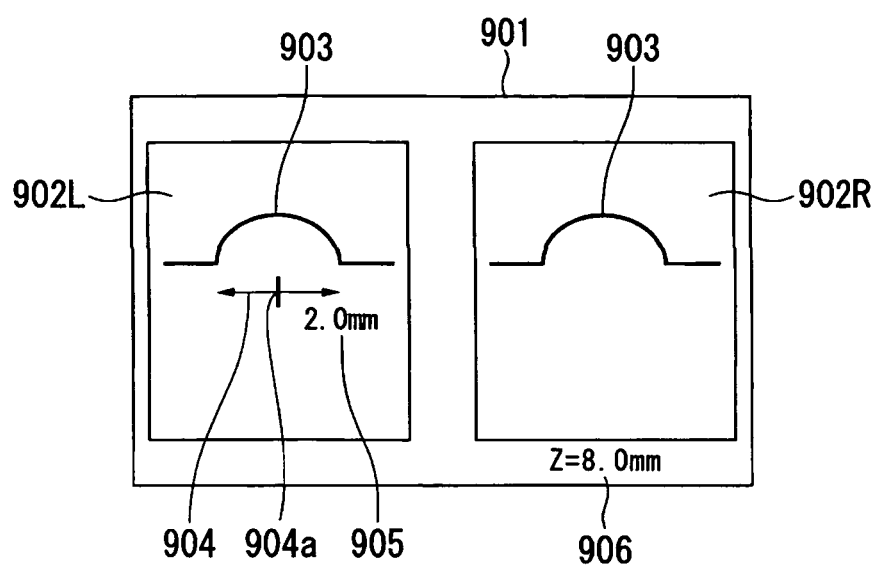
FIG. 9 is a reference diagram showing a display example of an endoscope image according to one embodiment of the present invention.
Figure 10A:
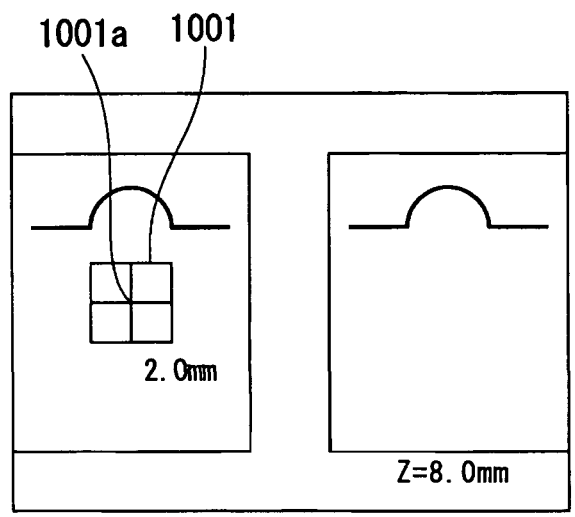
FIG. 10A is a reference diagram showing another display example of an endoscope image according to one embodiment of the present invention.
Figure 10B:
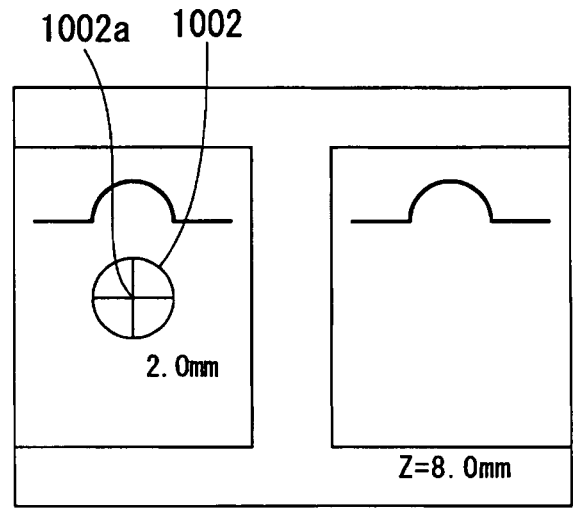
FIG. 10B is a reference diagram showing a further display example of an endoscope image according to one embodiment of the present invention.
Figure 10C:
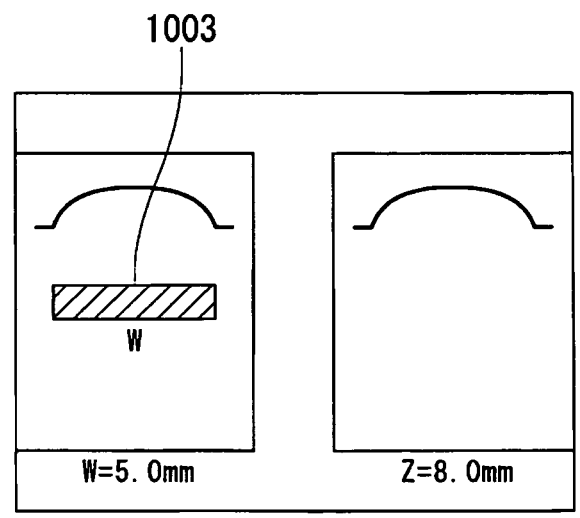
FIG. 10C is a reference diagram showing a still further display example of an endoscope image according to one embodiment of the present invention.

A display example of an endoscope image in the embodiment will be described next. In FIG. 9, a right image 902R and a left image 902L are displayed in a display screen 901 of the LCD 5 or the FMD 6. An object 903 is shown in those images. A mark 904 is displayed in the left image 902L. The lateral width of the left image 902L is equivalent to A in FIG. 8, and the length of the arrow of the mark 904 is equivalent to B in FIG. 8. Therefore, the actual length on the object equivalent to the length of the arrow of the mark 904 can be calculated from the equations 3 and 4.

The length of the mark is displayed as a mark length display character 905. The object distance is displayed as a distance display character 906. The user can easily know the size of the object by comparing the displayed object 903 and mark 904 with each other. The mark 904 in FIG. 9 serves as a sight indicating the object distance measuring point of the object distance. A center point 904a of the mark 904 is a sight. Information can be displayed in a small space by displaying the mark 904 over the sight as shown in FIG. 9.

FIGS. 10A to 11B show other display examples of an endoscope image. The shape of the mark is not limited to the one shown in FIG. 9, and may be the shape of a mark 1001 shown in FIG. 10A, the shape of a mark 1002 shown in FIG. 10B, or the shape of a mark 1003 shown in FIG. 10C. The centers, 1001a and 1002a, of the marks 1001 and 1002 are sights. The center of the mark 1003 is also a sight.

Figure 11A:
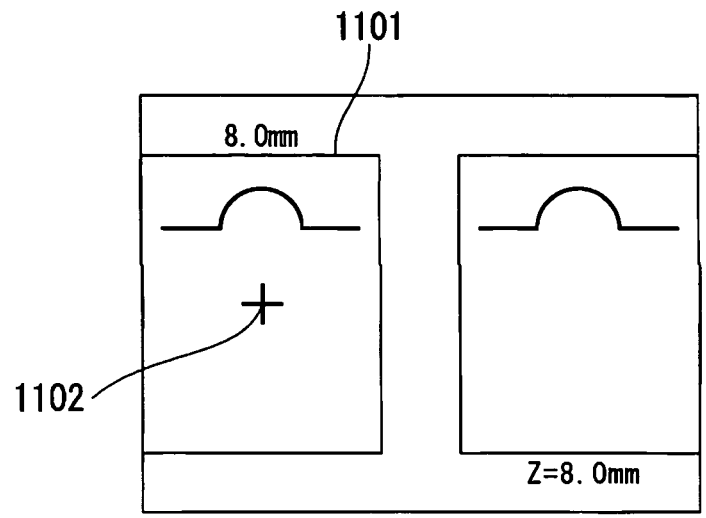
FIG. 11A is a reference diagram showing a still further display example of an endoscope image according to one embodiment of the present invention.
Figure 11B:
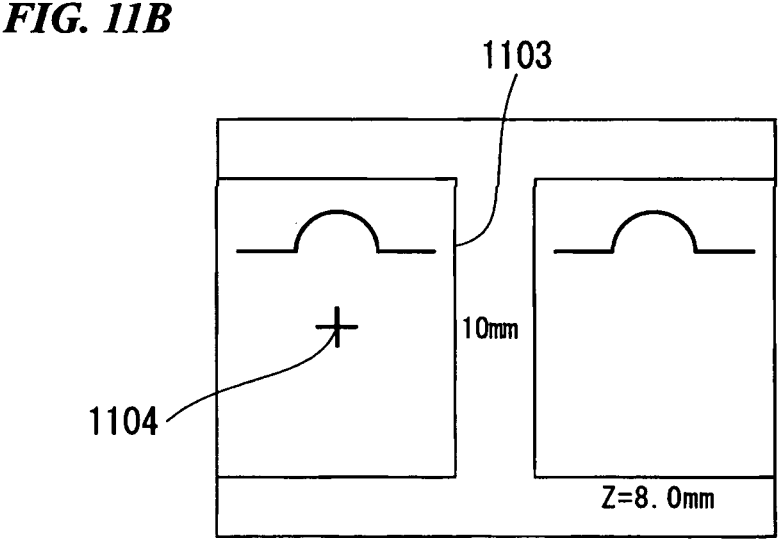
FIG. 11B is a reference diagram showing a still further display example of an endoscope image according to one embodiment of the present invention.

Further, a mark and a sight may be displayed separately, as indicated by a mark 1101 and a sight 1102 in FIG. 11A and a mark 1103 and a sight 1104 in FIG. 11B. When a mark and a sight are displayed separately this way, the position of the sight can be displayed explicitly. A mark may be displayed around the frame of an object image as indicated by the marks 1101 and 1103.

Next, specific procedures of the object measuring process in the embodiment will be described. First, procedures of a first operation example of this embodiment will be described referring to FIG. 12. In the first operation example, the display size of a mark is fixed. The object measuring process is activated by setting the zoom lever 47 to a wide end side under the following activation conditions.

(A) The optical adapter is set to a stereo optical adapter.

(B) A live image display or freeze image display is in progress.

(C) The electronic zooming is a wide end (electronic zooming is 1×).

When the object measuring process is activated, the CPU 18 operates according to the following procedures. First, an initialization process (step S100) is executed, then it is determined whether the operation mode of the endoscope apparatus 1 is a measuring mode or not (step S110). When the operation mode is other than the measuring mode, the object measuring process is terminated. When the operation mode is the measuring mode, it is determined whether or not a measurement cursor lies within a measurable area (step S120). When the measurement cursor lies outside the measurable area, a warning display process is executed (step S130), and the object measuring process is terminated.

Figure 13:
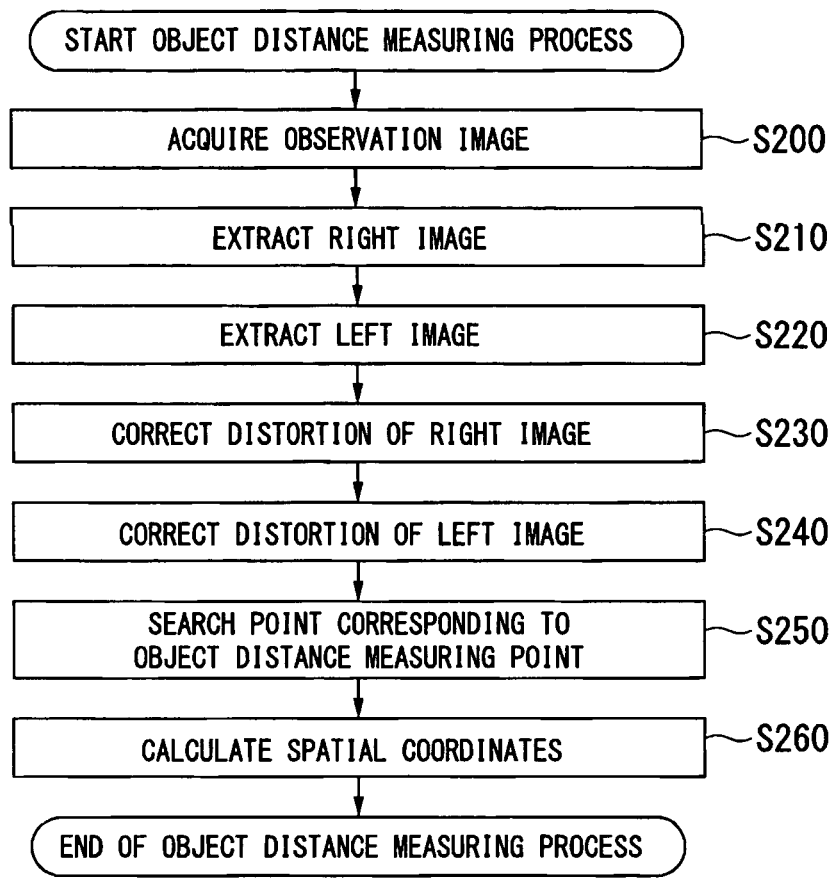
FIG. 13 is a flowchart illustrating procedures of the object measuring process (first operation example) according to one embodiment of the present invention.
Figure 14:
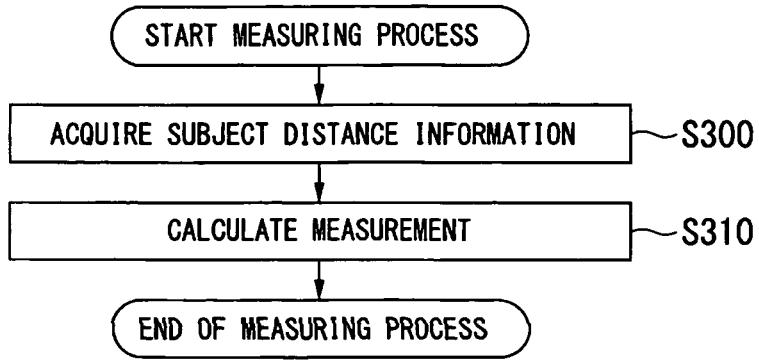
FIG. 14 is a flowchart illustrating procedures of the object measuring process (first operation example) according to one embodiment of the present invention.

When the measurement cursor lies within the measurable area, a measuring process shown in FIG. 13 is executed to calculate the object distance at the object distance measuring point (step S140). Subsequently, a measuring process shown in FIG. 14 is executed to calculate a mark's distance on the object corresponding to a predetermined display size of the mark (step S150), and a display process for the object distance and the mark is executed (step S160). After displaying the measuring results, it is determined whether or not there is a termination operation by the user (step S170). When there is the termination operation, the object measuring process is terminated. When there is no termination operation, the process returns to step S140 to resume the process.

Figure 12:
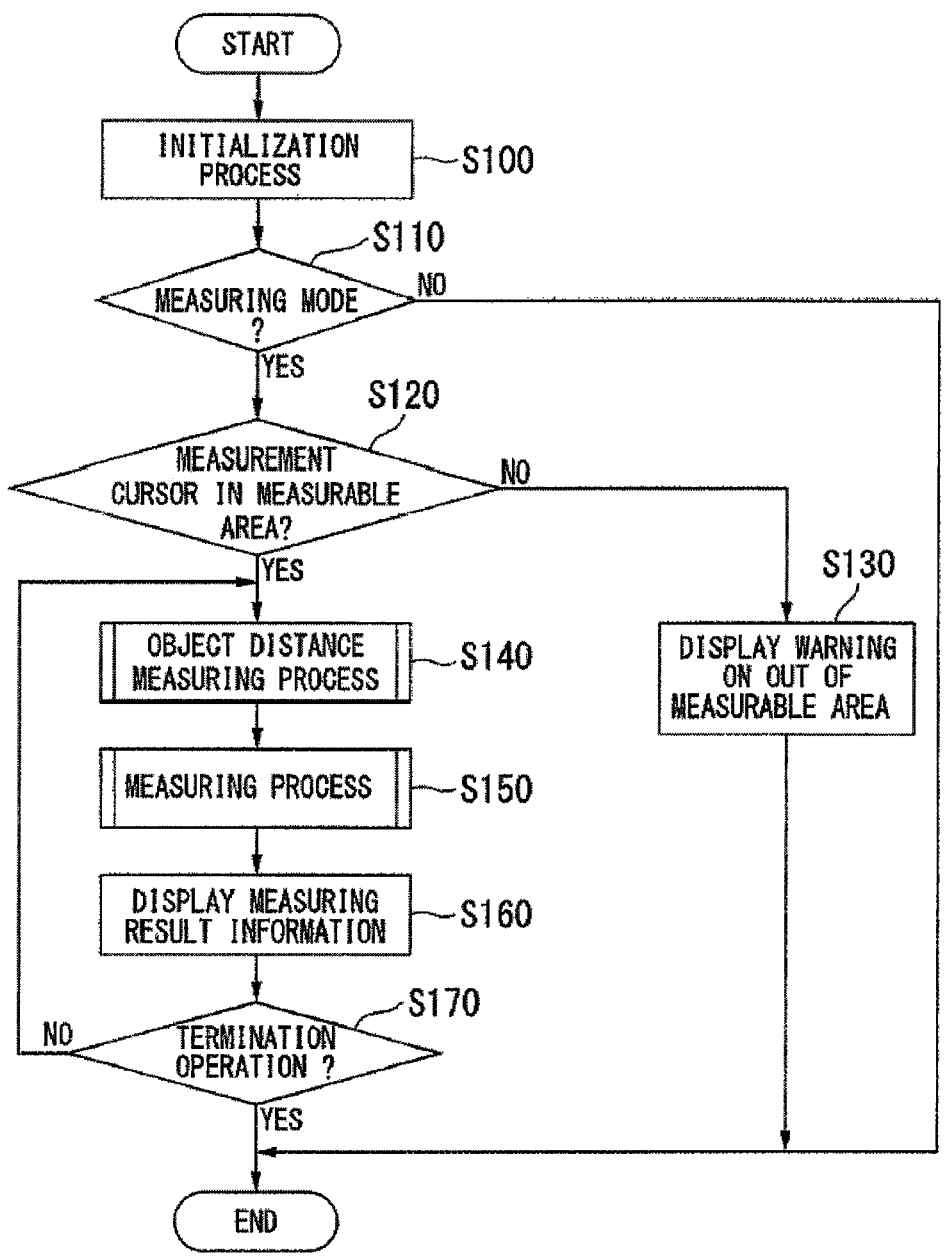
FIG. 12 is a flowchart illustrating procedures of an object measuring process (first operation example) according to one embodiment of the present invention.

FIG. 13 shows the details of step S140 in FIG. 12. The CPU 18 acquires image data from the video signal processing circuit 12 and stores the data in the RAM 14 (step S200). Subsequently, the CPU 18 executes a process of extracting a right image from an observation image indicated by the image data (step S210) and a process of extracting a left image therefrom (step S220). In general, an image formed by a lens system has optical distortion, which is a significant error factor in executing measuring. The CPU 18 executes a process of canceling the distortion from each image (steps S230, S240).

Then, the CPU 18 acquires the correlation between the left image and the right image by pattern matching with the center position of the sight being the object distance measuring point in the left image to search a point corresponding to the object distance measuring point from the right image (step S250). Subsequently, the CPU 18 calculates the spatial coordinates of the object distance measuring point based on the principle of triangulation based on the equations 1 and 2 to acquire the distance to the object distance measuring point (object distance) (step S260). The acquired object distance is stored in the RAM 14.

FIG. 14 shows the details of step S150 in FIG. 12. The CPU 18 reads the object distance calculated in step S260 in FIG. 13 from the RAM 14 (step S300), and calculates the value of Y in the equation 3 (step S310). At this time, the value of Y may be acquired from an arithmetic operation based on the equations 3 and 4, or may be acquired based on values in a table. The use of a table can reduce the amount of calculation and speed up the process.

FIG. 15 shows an example of the table. The values of Y for the values of X and θ in the equation 3 are acquired beforehand and a table associating the individual values is stored in one of the ROM 13, the PCMCIA memory card 32 and the flash memory card 33 beforehand. At the time of executing the object measuring process, the table is read from one of the memories and is stored in the RAM 14. The CPU 18 calculates the value of θ2 based on the equation 4, and reads the value of Y corresponding to the values of X and θ from the table with the value of θ2 taken as the value of θ. The table may be structured as a look-up table. A table also containing the value of A or the value of B may be prepared.

Figure 16A:
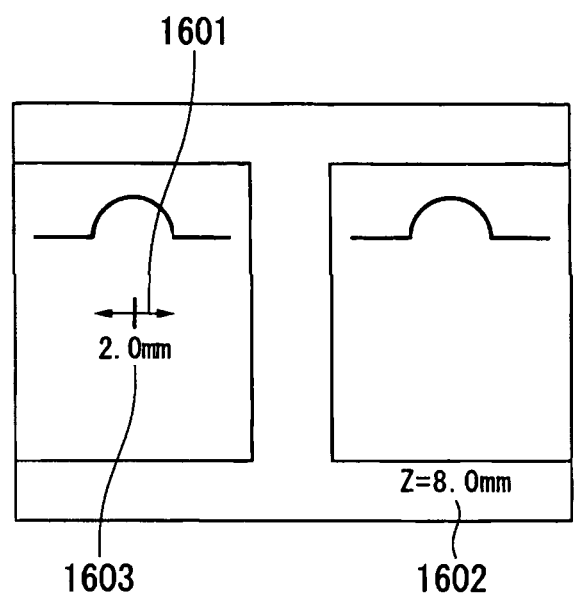
FIG. 16A is a reference diagram showing a display example of an endoscope image according to the object measuring process (first operation example) according to one embodiment of the present invention.
Figure 16B:
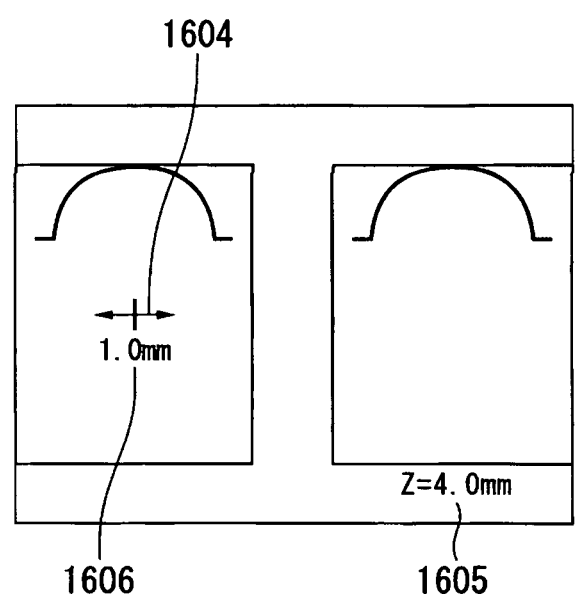
FIG. 16B is a reference diagram showing a display example of an endoscope image according to the object measuring process (first operation example) according to one embodiment of the present invention.

FIGS. 16A and 16B show display examples of an endoscope image when the object measuring process is executed.

When the distance to the object becomes closer with an image as shown in FIG. 16A being displayed, an image as shown in FIG. 16B is displayed. The display sizes of a mark 1601 in FIG. 16A and a mark 1604 in FIG. 16B are not changed. When the object distance becomes a half as indicated by the values of distance display characters 1602 and 1605, however, the distance on the object equivalent to the length of the mark also becomes a half as indicated by the values of mark length display characters 1603 and 1606. This is because with B being constant in the equations 3 and 4, when X becomes a half, Y becomes a half too.

Next, procedures of a second operation example of this embodiment will be described referring to FIG. 17. In the first operation example, the sight indicating the object distance measuring point is fixed in the center of the observation image, whereas in the second operation example, measurement is possible even when a sight moves on an observation image. The user can move the sight up and down and right and left on the screen by manipulating the lever switch 42 of the remote controller 4.

The aforementioned equations 3 and 4, which are satisfied when a sight is at the center of an observation image, are approximately satisfied even when the sight is off the center of the observation image. It is to be noted however that as the sight moves away from the center of the observation image, an error becomes greater. In a case where the user need not know the exact size of the object and a certain tentative size is sufficient, the use of the equations 3 and 4 is sufficiently practical.

Figure 17:
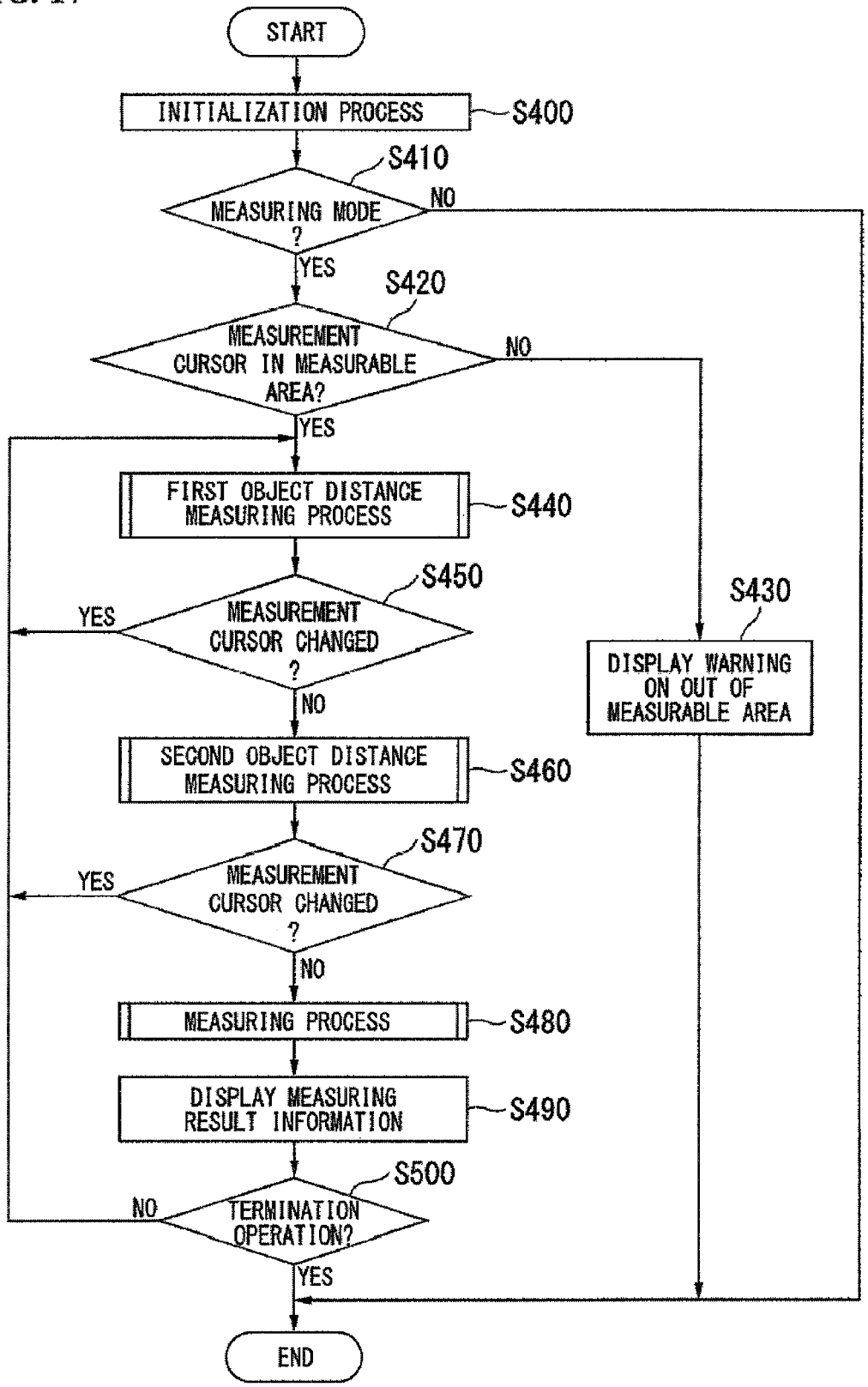
FIG. 17 is a flowchart illustrating procedures of an object measuring process (second operation example) according to one embodiment of the present invention.
Figure 18:
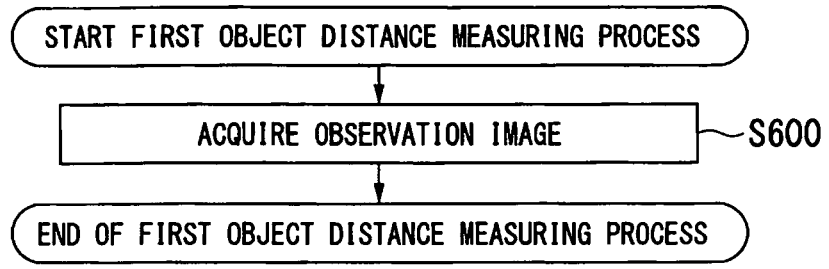
FIG. 18 is a flowchart illustrating procedures of the object measuring process (second operation example) according to one embodiment of the present invention.

Because steps S400 to S430 in FIG. 17 are the same as steps S100 to S130 in FIG. 12, their descriptions are omitted. When the measurement cursor lies within the measurable area in step S420, the CPU 18 executes a first distance-measuring process shown in FIG. 18 (step S440). In the first distance-measuring process, as shown in FIG. 18, the CPU 18 acquires image data from the video signal processing circuit 12 and stores the data in the RAM 14 (step S600).

This process is the same as the process of step S200 in FIG. 13.

Figure 19:
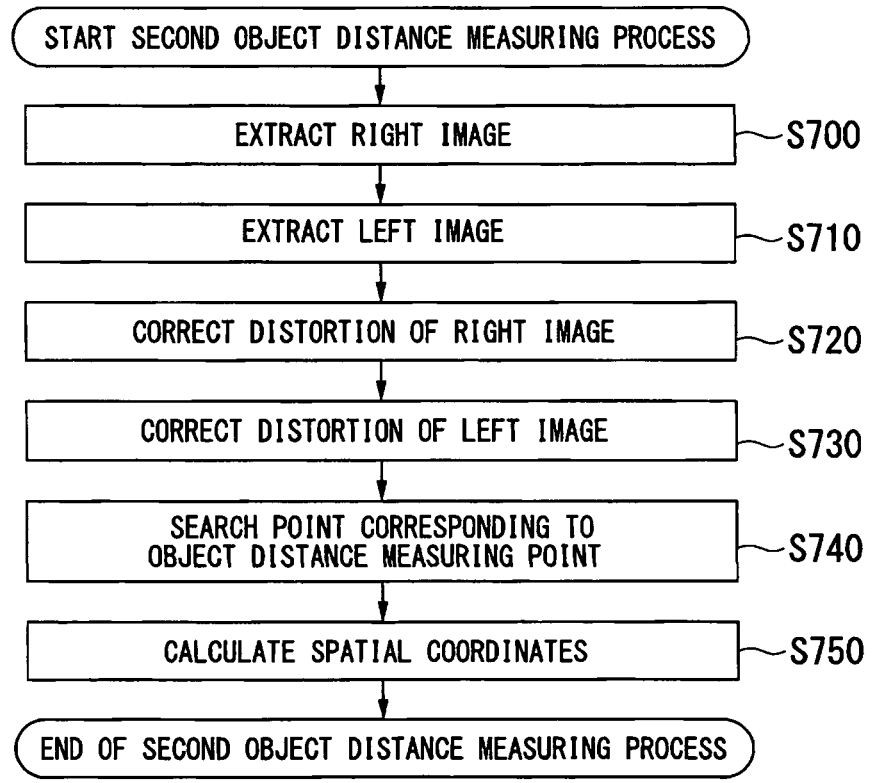
FIG. 19 is a flowchart illustrating procedures of the object measuring process (second operation example) according to one embodiment of the present invention.

Subsequently, the CPU 18 determines whether the measurement cursor has moved around step S440 or not (step S450). When the measurement cursor has moved, the process returns to step S440. When the measurement cursor has not moved, the CPU 18 executes a second distance-measuring process shown in FIG. 19 (step S460). Because steps S700 to S750 in the second distance-measuring process shown in FIG. 19 are the same as steps S210 to S260 in FIG. 13, their descriptions are omitted.

Then, the CPU 18 determines whether the measurement cursor has moved around step S460 or not (step S470). When the measurement cursor has moved, the process returns to step S440. When the measurement cursor has not moved, the CPU 18 executes the measuring process shown in FIG. 14 to calculate the mark's distance on the object corresponding to a predetermined display size of the mark (step S480).

Subsequently, a display process for the object distance and the mark is executed (step S490). After displaying the measuring results, it is determined whether or not there is a termination operation by the user (step S500). When there is the termination operation, the object measuring process is terminated. When there is no termination operation, the process returns to step S440 to resume the process.

Next, procedures of a third operation example of this embodiment will be described referring to FIG. 20. The display size of a mark is fixed in the first and second operation examples and the mark's size on the object changes according to the object distance, whereas in the third operation example, the mark's size on the object is fixed and the display size of the mark changes according to the object distance. The user can enter the tentative size on the object through, for example, the personal computer 31.

Figure 20:
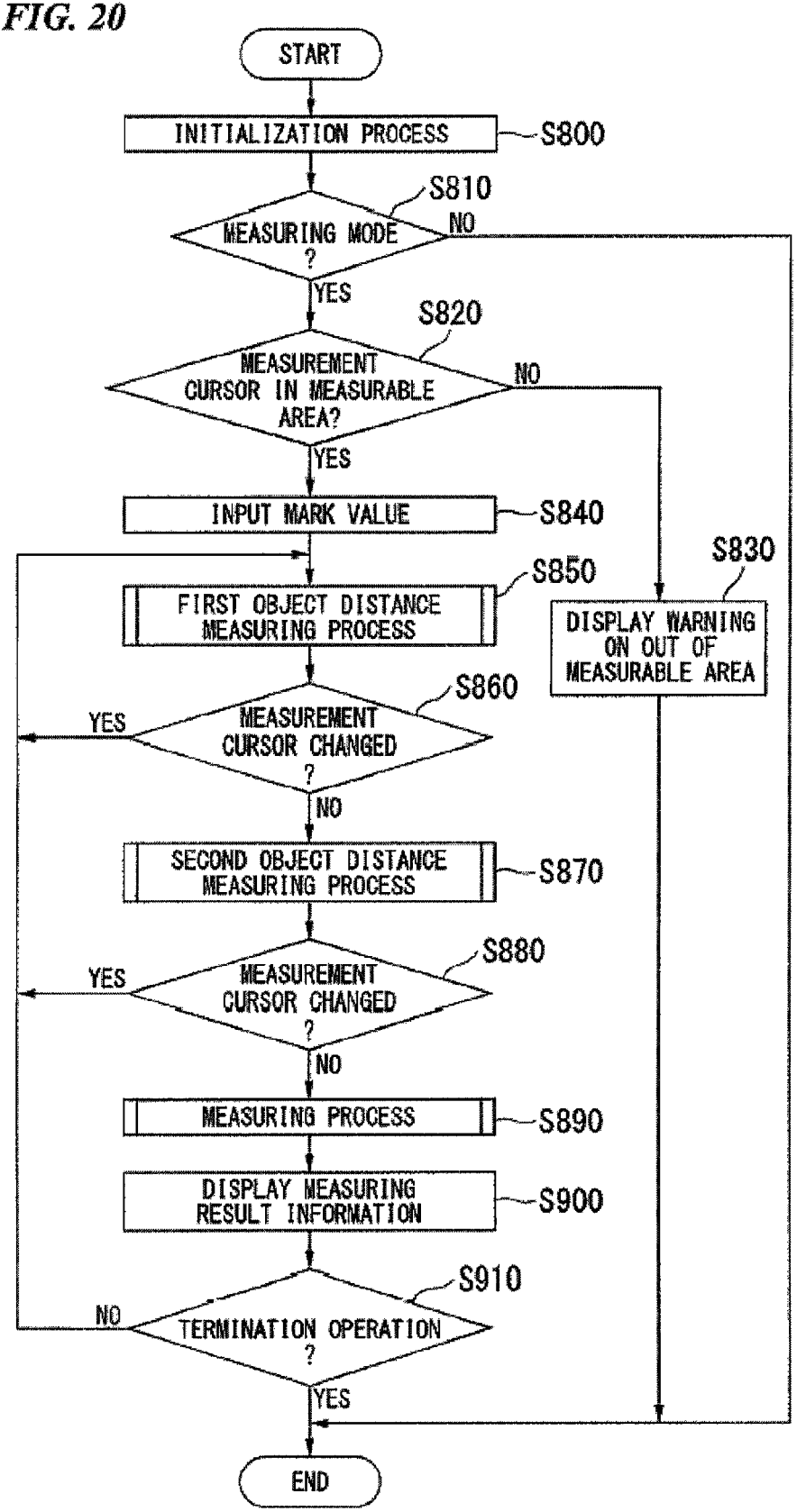
FIG. 20 is a flowchart illustrating procedures of an object measuring process (third operation example) according to one embodiment of the present invention.

Because steps S800 to S830 in FIG. 20 are the same as steps S100 to S130 in FIG. 12, their descriptions are omitted. When the measurement cursor lies within the measurable area in step S820, the CPU 18 reads and acquires information on the mark's size on the object, input through the USB I/F 16 and stored in the RAM 14, from the RAM 14 (step S840).

Subsequently, the CPU 18 executes the first distance-measuring process shown in FIG. 18 (step S850), and then determines whether the measurement cursor has moved around step S850 or not (step S860). When the measurement cursor has moved, the process returns to step S850. When the measurement cursor has not moved, the CPU 18 executes the second distance-measuring process shown in FIG. 19 (step S870).

Figures 21, 22:
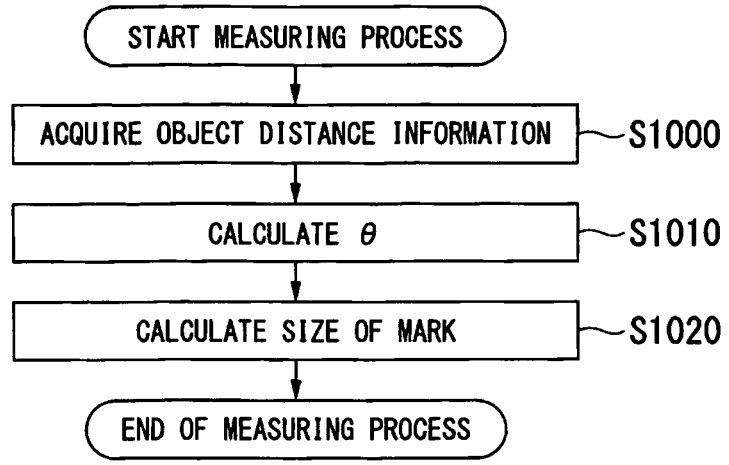
FIG. 21 is a flowchart illustrating procedures of the object measuring process (third operation example) according to one embodiment of the present invention.
FIG. 22 is a reference diagram showing the contents of a table used in the object measuring process (third operation example) according to one embodiment of the present invention.

Then, the CPU 18 determines whether the measurement cursor has moved around step S870 or not (step S880). When the measurement cursor has moved, the process returns to step S850. When the measurement cursor has not moved, the CPU 18 executes a measuring process shown in FIG. 21 (step S890). In the measuring process, as shown in FIG. 21, the CPU 18 reads and acquires the object distance, calculated in step S750 in FIG. 19, from the RAM 14 (step S1000). Then, the CPU 18 calculates the value of θ given by the following equation (step S1010). Changing the equation 3 for θ yields the following equation.

$$\theta = \tan^{-1}(Y/X) \quad (5)$$

θ is acquired by substituting the object distance X calculated in step S750 in FIG. 19 and the mark's distance Y on the object acquired in step S840 into the equation 5. At this time, the value of θ may be acquired through an arithmetic operation based on the equation 5 or may be acquired based on values in a table. The use of a table can reduce the amount of calculation and speed up the process.

FIG. 22 shows an example of the table. The values of θ for the values of X and Y in the equation 5 are acquired beforehand and a table associating the individual values is stored in one of the ROM 13, the PCMCIA memory card 32 and the flash memory card 33 beforehand. At the time of executing the object measuring process, the table is read from one of the memories and is stored in the RAM 14. The CPU 18 reads the value of θ corresponding to the values of X and Y from the table.

Following step S1010, the CPU 18 calculates the value of B given by the following equation (step S1020). Changing the equation 4 for B yields the following equation.

$$B = \theta \times A/\theta 1 \qquad (6)$$

B indicating the display size of the mark is acquired by substituting the previously-known view angle θ1 of the stereo optical adapter and A into the equation 6. The above-described table may be structured as a look-up table. A table further containing the value of A or the value of θ1 may be prepared.

Following the measuring process, a display process for the object distance and the mark is executed (step S900). After displaying the measuring results, it is determined whether or not there is a termination operation by the user (step S910). When there is the termination operation, the object measuring process is terminated. When there is no termination operation, the process returns to step S850 to resume the process.

Figure 23A:
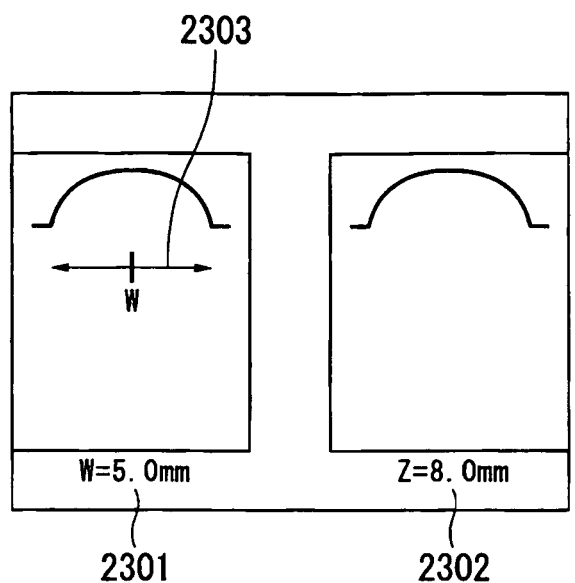
FIG. 23A is a reference diagram showing a display example of an endoscope image according to the object measuring process (third operation example) according to one embodiment of the present invention.
Figure 23B:
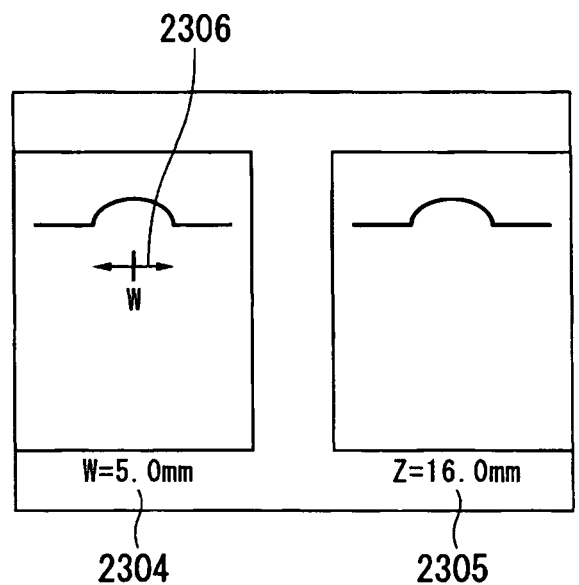
FIG. 23B is a reference diagram showing a display example of an endoscope image according to the object measuring process (third operation example) according to one embodiment of the present invention.

FIGS. 23A and 23B show display examples of an endoscope image when the above-described object measuring process is executed.

When the distance to the object becomes longer with an image as shown in FIG. 23A being displayed, an image as shown in FIG. 23B is displayed. The values of a mark length display character 2301 in FIG. 23A and a mark length display character 2304 in FIG. 23B are not changed. When the object distance changes as indicated by the values of distance display characters 2302 and 2305, however, the display length of the mark also changes as indicated by marks 2303 and 2306. This is because with Y being constant in the equations 5 and 6, when X changes, B changes too.

According to the embodiment, as described above, the size of a mark is calculated based on the object distance and the view angle of the endoscope and the mark is displayed along with the image of the object, so that the size of the object can be notified to the user in real time.

The mark's distance on the object can be changed according to the object distance without changing the display size of the mark as shown in FIG. 16 by calculating the mark's size on the object at a position apart by the object distance as in the first and second operation examples. In the mode where the display size of the mark is changeable, the object distance may become too short so that the mark cannot be fitted in the display area, or, on the other hand, the object distance may become too long so that the mark becomes too small on the display. However, fixing the display size of the mark can make it easier to always compare the object with the mark.

The display size of the mark can be changed according to the object distance without changing the size of the mark on the object as shown in FIGS. 23A and 23B by calculating the display size of the mark as in the third operation example. It is easier for the user to image the size of the object by comparing a predetermined length (e.g., 1 mm) with the size of the object, so that fixing the mark's size on the object can make it easier to see the size of the object.

According to this embodiment, the size of the mark is calculated based on the object distance and the view angle of the endoscope and the mark is displayed along with the image of the object, so that the size of the object can be notified to the user in real time.

Another embodiment of the present invention will be described referring to the accompanying drawings. In the following description, like or same reference numerals are given to those members which have structures similar to those of the members shown in FIGS. 1 to 6 and their descriptions are omitted.

Figure 24:
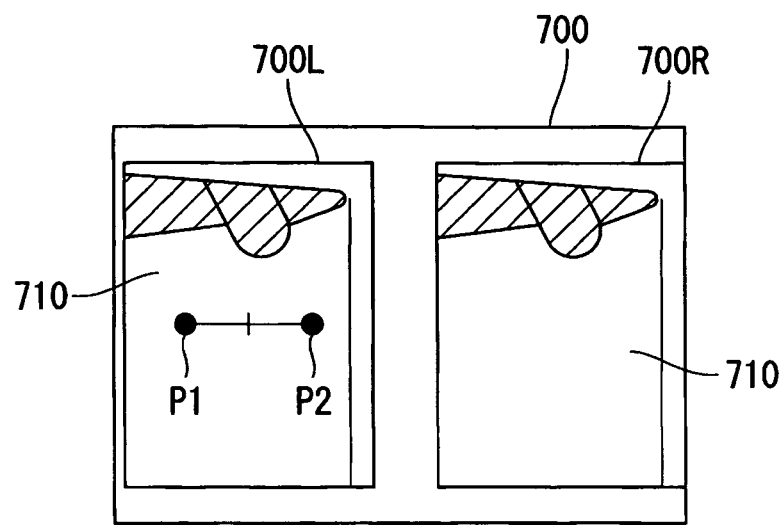
FIG. 24 is a reference diagram showing a display screen according to another embodiment of the present invention.

Display examples of an endoscope image and a mark in the embodiment will be described next. FIG. 24 shows a display screen for setting a mark which indicates the size of an object and the inclination of the object in the direction of the width of the image. In FIG. 24, a right image and a left image are respectively displayed in measurable areas 700R and 700L set on a display screen 700 of the LCD 5 or the FMD 6. The object 710 is displayed in these images.

The user first enters the positions of two points P1 and P2 on the object 710 to be reference points of the mark in the left image by manipulating the lever switch 42 of the remote controller 4 while watching the display screen 700. It is assumed that on the object 710, the point P1 is in front of the point P2, and the point P2 is at the back of the point P1. The spatial distance between the points P1, P2 tentatively represents the real size of the object 710.

Figure 25A:
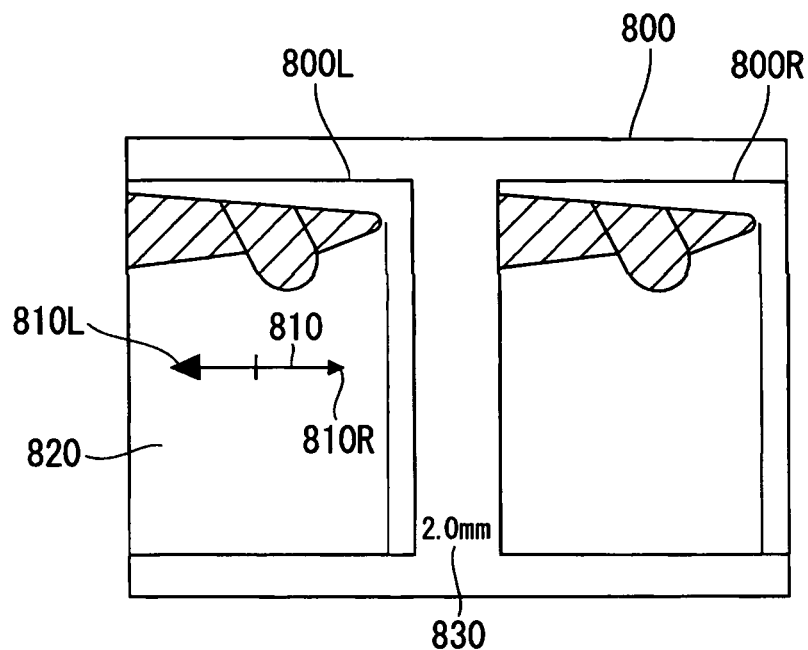
FIG. 25A is a reference diagram showing a display screen according to another embodiment of the present invention.
Figure 25B:
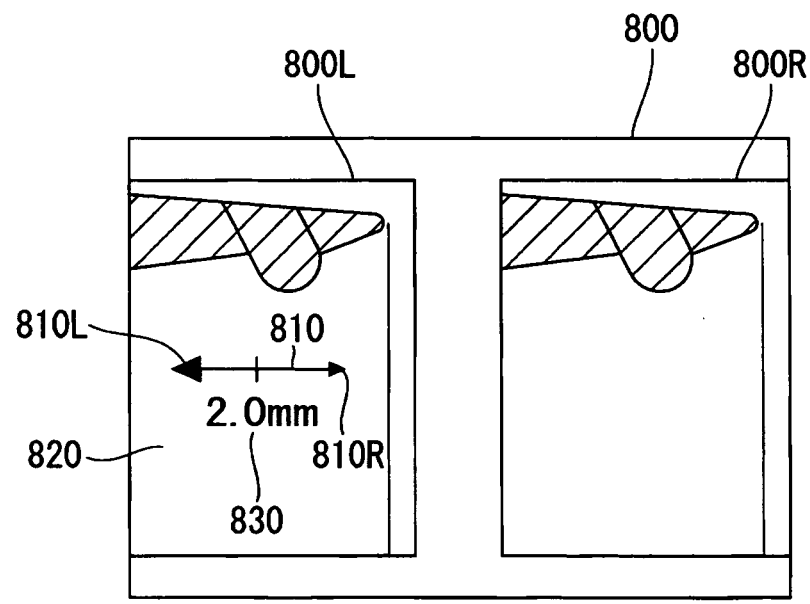
FIG. 25B is a reference diagram showing a display screen according to another embodiment of the present invention.

FIGS. 25A and 25B show display screens having marks displayed thereon. A right image and a left image are respectively displayed in measurable areas 800R and 800L set on a display screen 800, with a mark 810 displayed on the left image. The mark 810 is displayed as an arrow. A left mark 810L of the arrow is displayed larger than a right mark 810R. The size of the mark represents the inclination of an object 820 in a depthwise direction of the image, and the user can know that the mark 810L is on the front side (near side) and the mark 810R is on the back side (far side).

The user can roughly know the size of the object 820 from a value 830. The value 830 represents the spatial distance between the two points P1, P2 shown in FIG. 24 and corresponds to the length of the mark 810 displayed as the arrow. Because the value 830 is displayed at a location other than the measurable area where the image of the object 820 is displayed in FIG. 25A, the object 820 is easier to see. Because the value 830 is displayed over the image of the object 820, the display space for the value can be set larger than that in FIG. 25A.

As the value 830 is displayed near the mark 810, the size of the object can be grasped more easily.

Although the value representing the spatial distance between the two points P1, P2 is given separate from a mark in the foregoing description, something which includes both a figure or the like representing a mark and a value representing the spatial distance between the two points P1, P2 may be taken as a single mark.

Figure 26A:
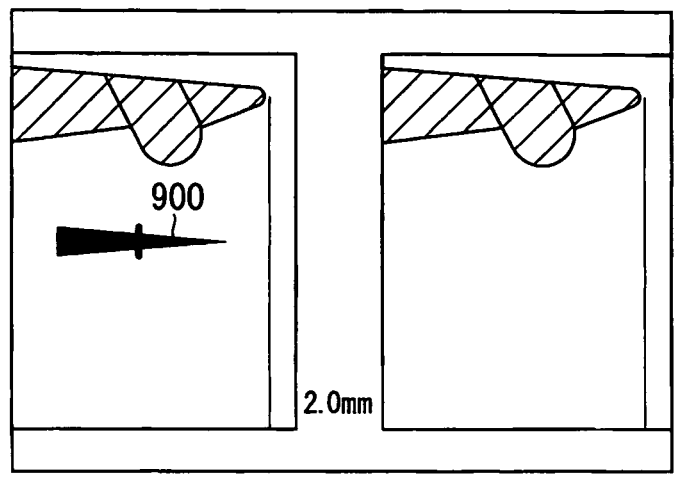
FIG. 26A is a reference diagram showing a display screen according to another embodiment of the present invention.
Figure 26B:
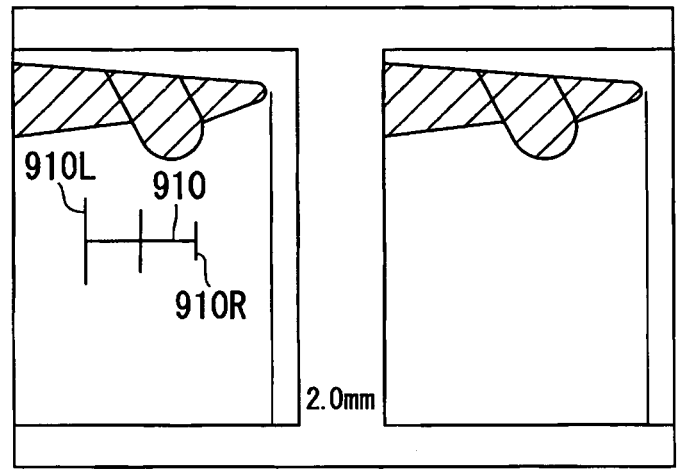
FIG. 26B is a reference diagram showing a display screen according to another embodiment of the present invention.
Figure 26C:
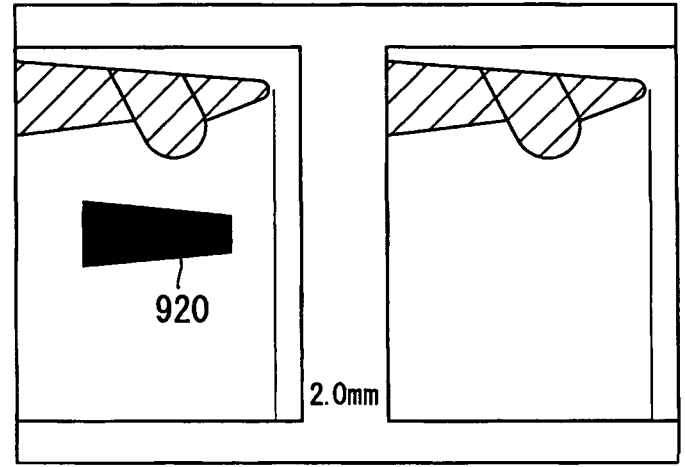
FIG. 26C is a reference diagram showing a display screen according to another embodiment of the present invention.

FIGS. 26A to 26C show other display examples of a mark. In FIG. 26A, the overall shape of a mark 900 is an arrow, and the direction of the arrow represents the inclination of an object. In FIG. 26B, the difference between the lengths of lines 910L, 910R of left and right images represents the inclination of the object. In FIG. 26C, a mark 920 has a quadrangular shape the difference between whose vertical widths represents the inclination of the object. The shape of a mark can be other than those shown in FIGS. 24 to 26C, for example, a polygonal shape or a circular shape. Although the two points P1, P2 are set side by side horizontally in FIG. 24, the set positions of the two points P1, P2 are optional and the direction of an arrow or the like can be changed according to the set positions.

Figure 27:
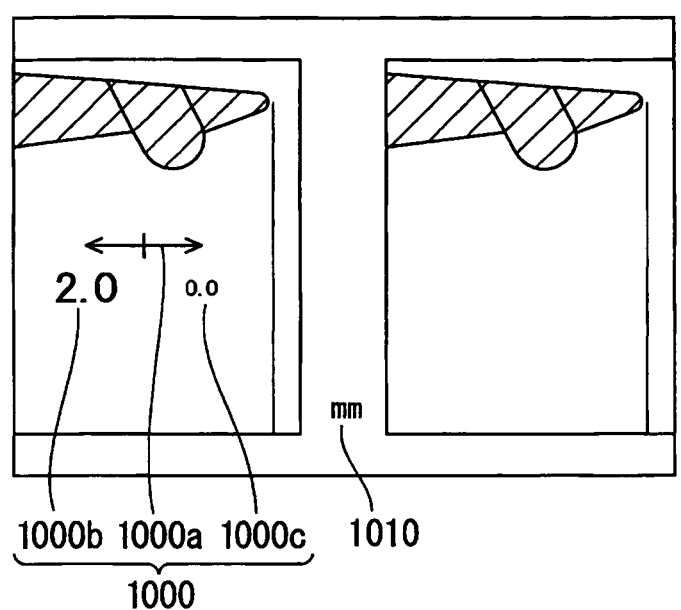
FIG. 27 is a reference diagram showing a display screen according to another embodiment of the present invention.

FIG. 27 shows another display example of a value indicating the size of an object. A mark 1000 includes an arrow 1000a indicating the size of the object, values 1000b and 1000c indicating the length of an arrow 1000a and the inclination of the object. A value 1010 indicating the unit of the length represented by the value 1000b, 1000c is displayed outside the measurable area. The spatial distance on the object which is equivalent to the length of the arrow 1000a is 2.0 mm. As the value 1000b is displayed larger than the value 1000c, the user can know that the left-hand side is on the front side (near side) and the right-hand side is on the back side (far side).

Figure 28:
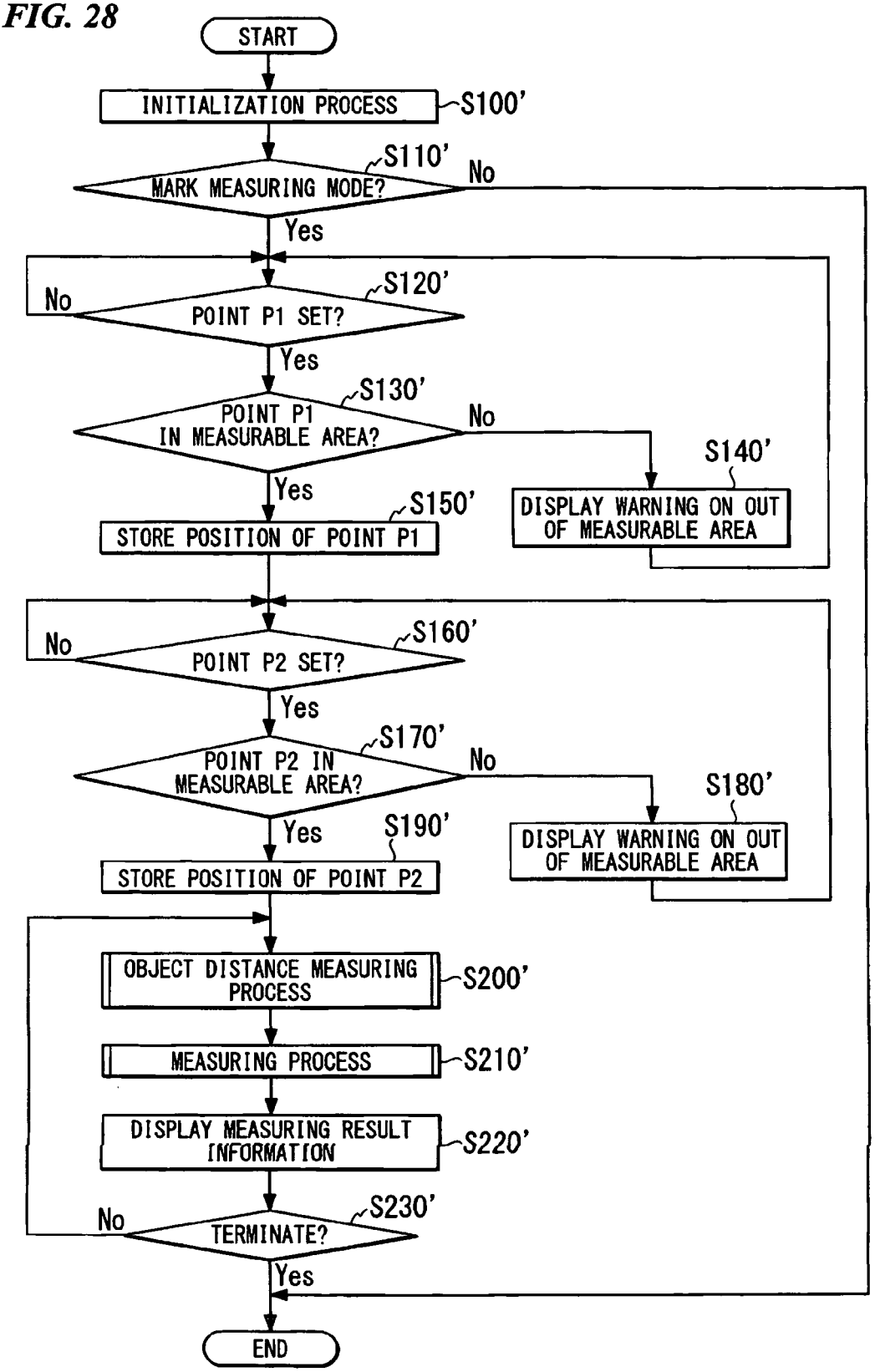
FIG. 28 is a flowchart illustrating procedures of the object measuring process (first operation example) according to another embodiment of the present invention.

Next, specific procedures of the object measuring process in the embodiment will be described. First, procedures of a first operation example of this embodiment will be described. In the first operation example, the display position of a mark is fixed. FIG. 28 shows procedures of the first operation example. When the measurement execution switch 45 of the remote controller 4 is operated to the ON side, the object measuring process is activated.

When the object measuring process is activated, the CPU 18 operates according to the following procedures. First, an initialization process (step S100') is executed, then it is determined whether the operation mode of the endoscope apparatus 1 is a mark measuring mode or not (step S110'). When the operation mode is other than the mark measuring mode, the object measuring process is terminated. When the operation mode is the mark measuring mode, the operation of the lever switch 42 of the remote controller 4 is monitored to determine whether the point P1 shown in FIG. 24 is set (step S120').

When the point P1 is not set, the process returns to step S120' to resume monitoring on the setting of the point P1. When the point P1 is set, it is determined whether or not the coordinates of the point P1 on the display screen lie within a measurable area (step S130'). When the coordinates of the point P1 on the display screen lie outside the measurable area, a warning display process is executed (step S140'), and the process returns to step S120' to execute monitoring of the point P1 again.

When the coordinates of the point P1 on the display screen lie within the measurable area, the coordinates of the point P1 on the display screen are stored in the RAM 14 (step S150'). Subsequently, the operation of the lever switch 42 of the remote controller 4 is monitored to determine whether the point P2 shown in FIG. 24 is set (step S160').

When the point P2 is not set, the process returns to step S160' to resume monitoring on the setting of the point P2. When the point P2 is set, it is determined whether or not the coordinates of the point P2 on the display screen lie within a measurable area (step S170'). When the coordinates of the point P2 on the display screen lie outside the measurable area, a warning display process is executed (step S180'), and the process returns to step S160' to execute monitoring of the point P2 again.

Figure 29:
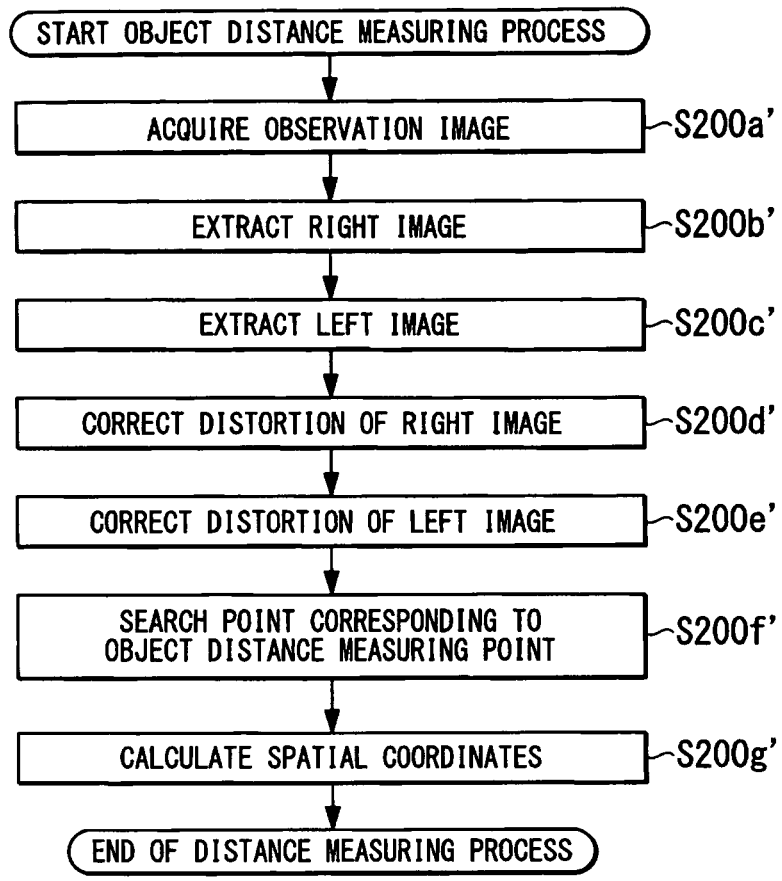
FIG. 29 is a flowchart illustrating procedures of the object measuring process (first operation example) according to another embodiment of the present invention.

When the coordinates of the point P2 on the display screen lie within the measurable area, the coordinates of the point P2 on the display screen are stored in the RAM 14 (step S190'). Subsequently, a distance-measuring process shown in FIG. 29 is executed to calculate the spatial coordinates of the points P1, P2 on the object and the object distances from the points P1, P2 to the image-forming surface of the endoscope 2 (step S200'). Then, the spatial distance between the points P1, P2 is calculated by executing the measuring process shown in FIG. 13 (step S210'), and a display process for the measuring results including the mark is executed (step S220'). Accordingly, the mark is displayed in display modes as shown in FIGS. 25A to 27. After displaying the measuring results, it is determined whether or not there is a termination operation by the user (step S230'). When there is the termination operation, the object measuring process is terminated. When there is no termination operation, the process returns to step S200' to resume the process.

FIG. 29 shows the details of step S200' in FIG. 28. The CPU 18 acquires image data from the video signal processing circuit 12 and stores the data in the RAM 14 (step S200a'). Subsequently, the CPU 18 executes a process of extracting a right image from an observation image indicated by the image data (step S200b') and a process of extracting a left image therefrom (step S200c'). In general, an image formed by a lens system has optical distortion, which is a significant error factor in executing measuring. The CPU 18 executes a process of canceling the distortion from each image (steps S200d', S200e').

Then, the CPU 18 acquires the correlation between the left image and the right image by pattern matching with the positions of the points P1, P2 being object distance measuring points in the left image to search a point corresponding to the object distance measuring point from the right image (step S200f'). Subsequently, the CPU 18 calculates the spatial coordinates of the object distance measuring point and the distances to the object distance measuring points (object distances) based on the principle of triangulation based on the equations 1 and 2 (step S200g'). Given that the spatial coordinates of the points P1, P2 on the object are (x1, y1, z1), (x2, y2, z2), respectively, the object distance at the point P1 becomes z1 and the object distance at the point P2 becomes z2. The spatial coordinates and the object distances calculated in step S200g' are stored in the RAM 14.

Figure 30:
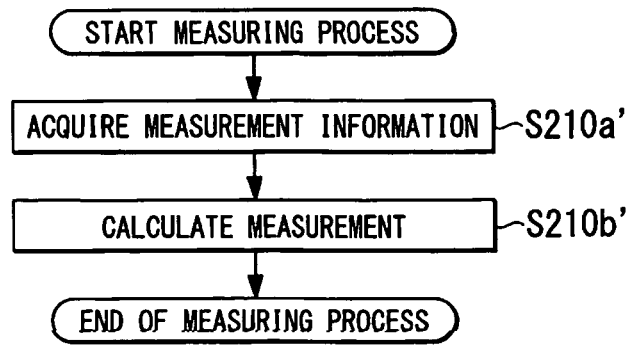
FIG. 30 is a flowchart illustrating procedures of the object measuring process (first operation example) according to another embodiment of the present invention.

FIG. 30 shows the details of step S210' in FIG. 28. The CPU 18 reads and acquires the spatial coordinates of the points P1, P2 calculated in step S200g' in FIG. 29 from the RAM 14 (step S210a'), and calculates a spatial distance L between the points P1, P2 from the following equation 3.

$$L=\sqrt{(x1-x2)^2+(y1-y2)^2+(z1-z2)^2} \qquad (3)$$

In step S220' in FIG. 28, the CPU 18 reads and acquires the object distances at the points P1, P2, calculated in step S200', from the RAM 14, and executes a mark display process based on the object distances and the spatial distance between the points P1, P2. More specifically, the CPU 18 compares the object distance at the point P1 with the object distance at the point P2, and executes a process of visualizing the inclination of the object based on the comparison result. When the inclination of the object is represented by arrows as shown in FIGS. 25A and 25B, for example, the arrow to be drawn at a point of a longer object distance is made large, while the arrow to be drawn at a point of a shorter object distance is made small. The CPU 18 executes a process of displaying a value of the spatial distance between the points P1, P2 near the mark or at another location. At the time of displaying the mark, the shape thereof may be set in consideration of the optical distortion of the image.

Figure 31:
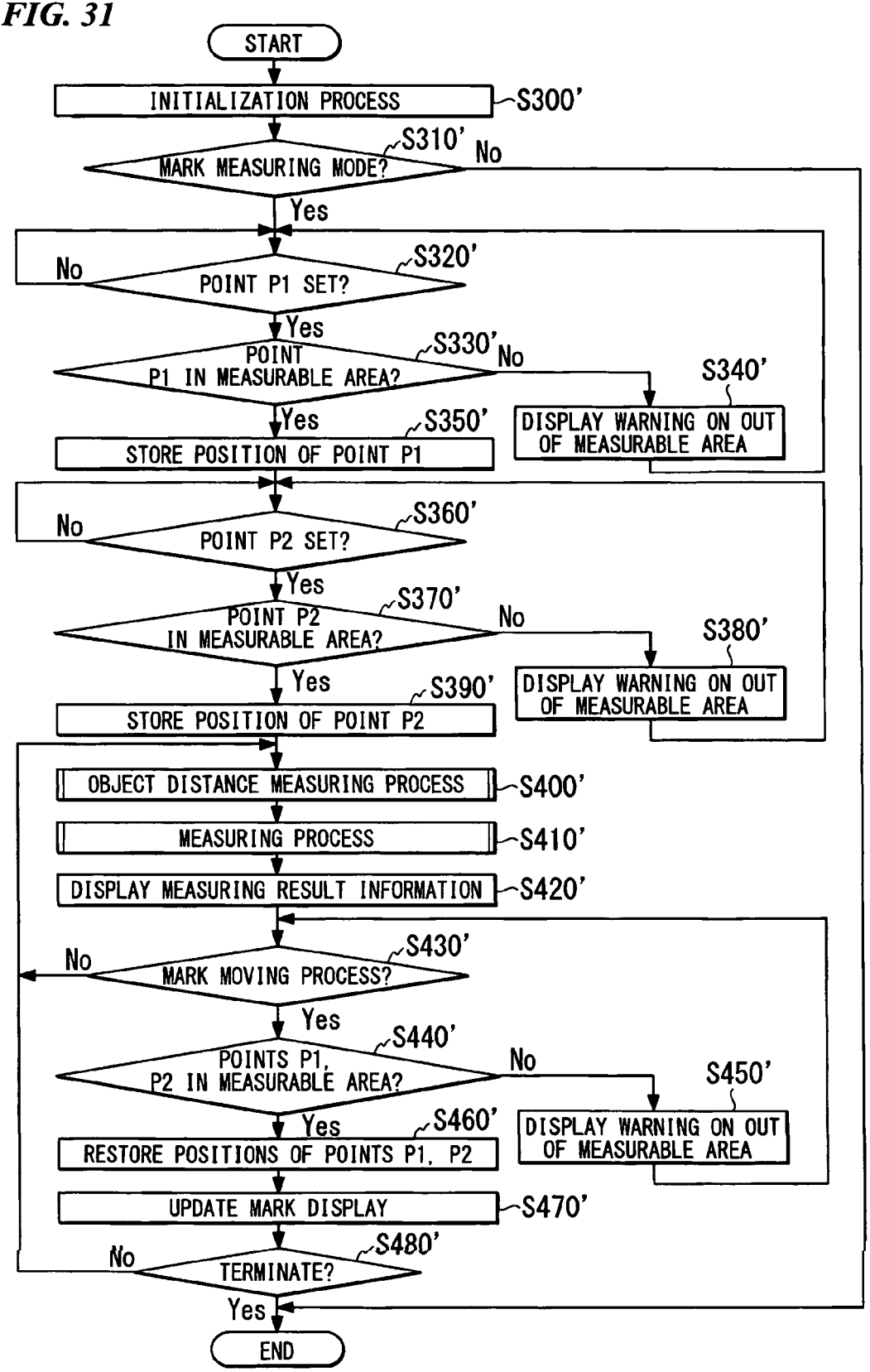
FIG. 31 is a flowchart illustrating procedures of the object measuring process (second operation example) according to another embodiment of the present invention.

Next, a second operation example of this embodiment will be described. In the second operation example, the user can move a mark on the display screen. FIG. 31 shows procedures of the second operation example. When the measurement execution switch 45 of the remote controller 4 is operated to the ON side, the object measuring process is activated.

When the object measuring process is activated, the CPU 18 operates according to the following procedures. Because processes of steps S300' to S420' are the same as the processes of steps S100' to S220' in FIG. 28, their descriptions are omitted. The details of the process of step S400' are the same as those of the process shown in FIG. 29, and details of the process of step S410' are the same as those of the process shown in FIG. 30.

Following step S420', the operation of the lever switch 42 of the remote controller 4 is monitored to determine whether the movement of the mark has been instructed (step S430'). When the movement of the mark has not been instructed, the process returns to step S400' to resume the process. When the movement of the mark has been instructed, the coordinates of the destinations of the movement of the points P1, P2 are calculated, and it is determined whether or not the coordinates of both the points P1, P2 on the display screen lie within the measurable area (step S440'). When the coordinates of at least one of the points P1, P2 on the display screen lie outside the measurable area, a warning display process is executed (step S450'), and the process then returns to step S430' to execute monitoring on the setting of the points P1, P2 again.

Figure 32:
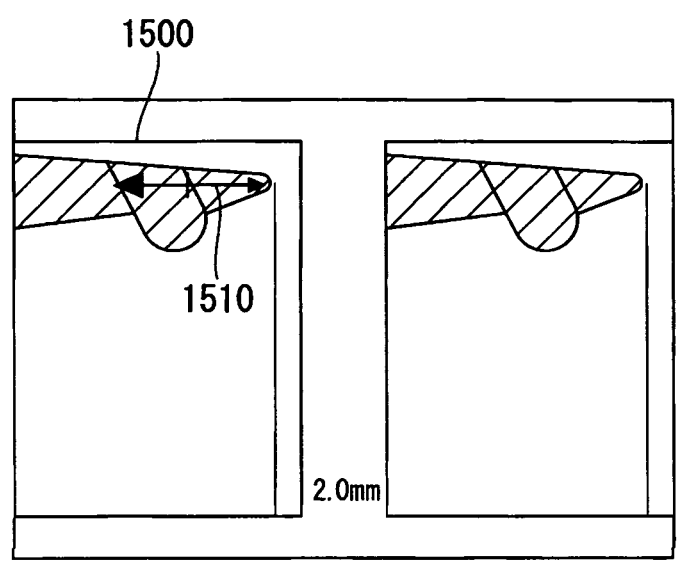
FIG. 32 is a reference diagram showing a display screen according to another embodiment of the present invention.

When the coordinates of both the points P1, P2 on the display screen lie within the measurable area, the coordinates of the points P1, P2 are stored in the RAM 14 (step S460'). A process of updating the display of the mark is executed to move the mark in the direction instructed by the user (step S470'). Subsequently, it is determined whether or not there is a termination operation by the user (step S470'). When there is the termination operation, the object measuring process is terminated. When there is no termination operation, the process returns to step S400' to resume the process. The foregoing processes can allow a mark 1510 to move freely in a measurable area 1500 as shown in FIG. 32.

Next, a third operation example of this embodiment will be described. In the first and second operation examples, the user enters the positions of the points P1, P2, whereas in the third operation example, the user enters the value of a spatial distance which the user wants to use as an indication.

Figure 36A:
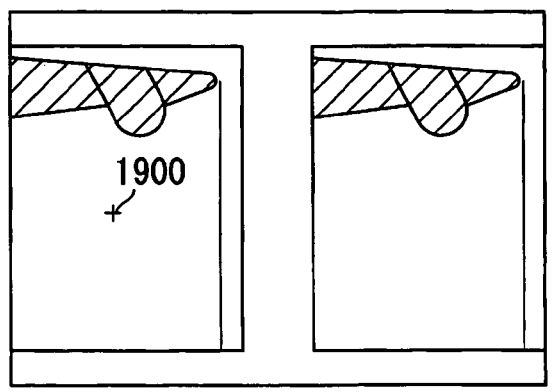
FIG. 36A is a reference diagram showing a display screen according to another embodiment of the present invention.
Figure 36B:
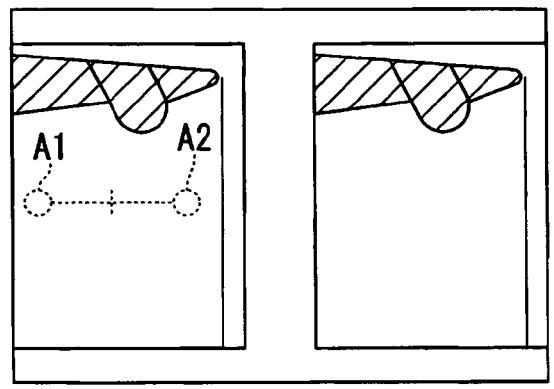
FIG. 36B is a reference diagram showing a display screen according to another embodiment of the present invention.

First, the third operation example will be described schematically referring to FIGS. 36A to 36D. FIG. 36A illustrates a display screen showing a sight 1900 to be a reference for the measuring position of an object, when the object measuring process is activated. In this state, the user enters the value of a spatial distance desirable as an indication. At this time, the length on the display screen which corresponds to the input spatial distance on the object is unclear, so that first, points A1, A2 are set at predetermined positions with the sight 1900 taken as a reference as shown in FIG. 36B. The points A1, A2 are not displayed on the actual display screen.

Figure 36C:
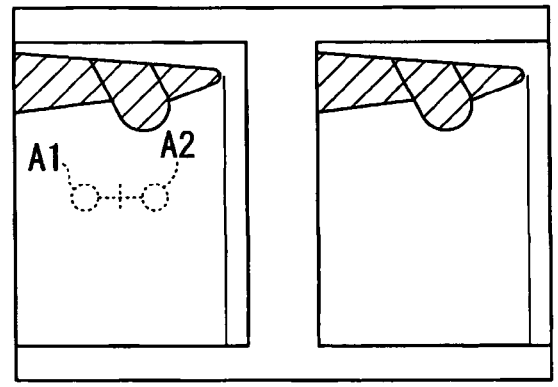
FIG. 36C is a reference diagram showing a display screen according to another embodiment of the present invention.
Figure 36D:
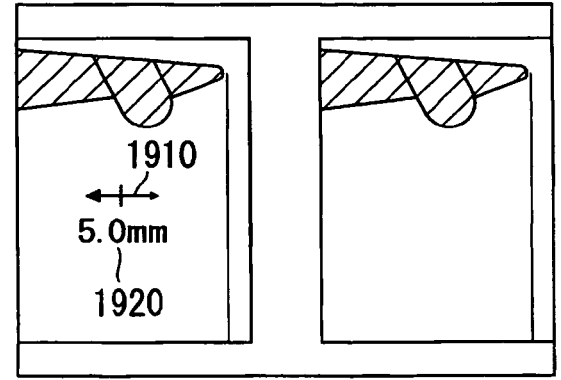
FIG. 36D is a reference diagram showing a display screen according to another embodiment of the present invention.

Subsequently, the spatial coordinates of the points A1, A2 on the object are calculated and the spatial distance between the points A1, A2 are calculated from the spatial coordinates of the points A1, A2 on the object, as done in the first and second operation examples. If the result of calculating the spatial distance between the preset points A1, A2 is 10 mm and the spatial distance input by the user is 5 mm, it is apparent that the distance between the points A1, A2 shown in FIG. 36B should be multiplied by ½(=5 mm/10 mm) and the points A1, A2 should be set as shown in FIG. 36C. FIG. 36D shows a final display screen with a mark 1910 and a value 1920 of the spatial distance being displayed thereon.

Figure 33:
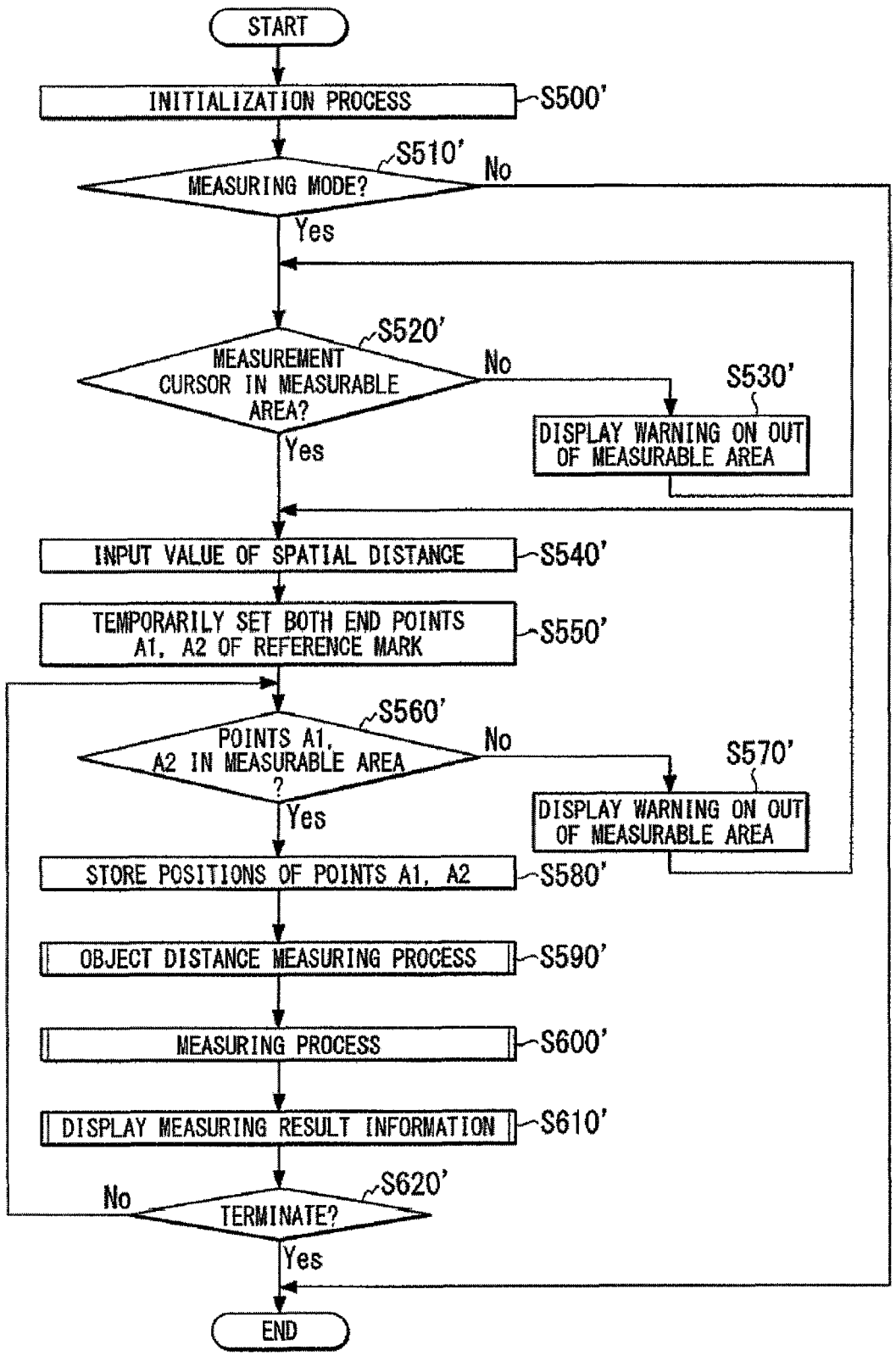
FIG. 33 is a flowchart illustrating procedures of the object measuring process (third operation example) according to another embodiment of the present invention.

The details of the third operation example will be described below. FIG. 33 shows procedures of the third operation example. When the measurement execution switch 45 of the remote controller 4 is operated to the ON side, the object measuring process is activated. When the object measuring process is activated, the CPU 18 operates according to the following procedures. In the object measuring process, the position of a sight in the display screen may be automatically determined by the apparatus or the user may designate an arbitrary sight position.

First, an initialization process (step S500') is executed, then it is determined whether the operation mode of the endoscope apparatus 1 is a mark measuring mode or not (step S510'). When the operation mode is other than the mark measuring mode, the object measuring process is terminated. When the operation mode is the mark measuring mode, the operation of the lever switch 42 of the remote controller 4 is monitored to determine whether the measurement cursor on the display screen to be displayed as a reference for the measuring position of the object lies within the measurable area (step S520').

When the measurement cursor on the display screen lies outside the measurable area, a warning display process is executed (step S530'), and the process returns to step S520' to execute monitoring of the sight again. When the measurement cursor on the display screen lies within the measurable area, the following process is executed. With the sight being positioned in the measurable area, the user can enter the value of the desirable spatial distance to be an indication. When the user enters the value of the spatial distance by operating the personal computer 31 (which may be the lever switch 42 of the remote controller 4), the CPU 18 stores the value in the RAM 14 (step S540').

Subsequently, the initial predetermined values on the positions of the points A1, A2 (e.g., predetermined values indicating distances of the points A1, A2 on the display screen) are read from the RAM 14, and the coordinates of the points A1, A2 on the display screen to be references are calculated based on the sight's coordinates on the display screen (step S550').

Accordingly, the points A1, A2 are temporarily set. Then, it is determined whether or not the coordinates of both the points A1, A2 on the display screen lie within the measurable area (step S560'). When the coordinates of at least one of the points A1, A2 on the display screen lie outside the measurable area, a warning display process is executed (step S570'), and the process then returns to step S540'.

When the coordinates of both the points A1, A2 on the display screen lie within the measurable area, the object distances to the image forming surface of the endoscope 2 from the spatial coordinates of the points A1, A2 on the object and the points A1, A2 are calculated (step S590'). The process of step S590' is the same as the process shown in FIG. 29.

Subsequently, the spatial distance between the points A1, A2 is calculated by executing a measuring process shown in FIG. 34 (step S600'). Further, a display process for the measuring results including the mark is executed by executing a result information display process shown in FIG. 35 (step S610'). Subsequently, it is determined whether or not there is a termination operation by the user (step S620'). When there is the termination operation, the object measuring process is terminated. When there is no termination operation, the process returns to step S560' to resume the process.

Figure 34:
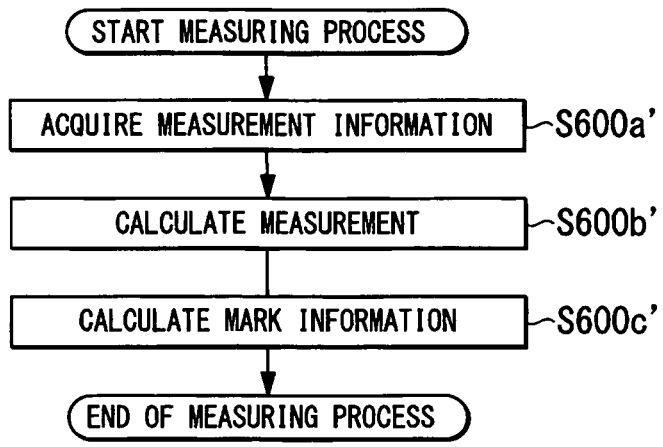
FIG. 34 is a flowchart illustrating procedures of the object measuring process (third operation example) according to another embodiment of the present invention.

FIG. 34 shows the details of step S600' in FIG. 33. The CPU 18 reads and acquires, from the RAM 14, the value of a spatial distance entered in step S540' in FIG. 33, the spatial coordinates of the points A1, A2 calculated in step S590', and the initial set values on the positions of the points A1, A2 on the display screen (step S600a'). Subsequently, the spatial distance between the points A1, A2 is calculated (step S600b'). Further, the coordinates of the points A1, A2 on the display screen to be reference points for both ends of the mark are calculated based on the input value of the spatial distance, the results of calculating the spatial distance between the points A1, A2, and the initial set values on the positions of the points A1, A2 on the display screen, and the calculated results are stored in the RAM 14 (step S600c').

In step S600c', for example, the ratio of the input value of the spatial distance (corresponding to 5 mm mentioned above), to the calculated values of the spatial distance between the initially-set points A1, A2 on the object (corresponding to 10 mm mentioned above) is calculated. Then, a distance L' on the display screen (image forming surface) corresponding to the input value of the spatial distance is calculated in such a way that the ratio of the distance L' to the initially set value of the distance between the points A1, A2 on the display screen (image forming surface) becomes equal to the former ratio. Then, with the position of the sight being the center, the coordinates of the points A1, A2 at which the distance between the points A1, A2 becomes L' are calculated.

Figure 35:
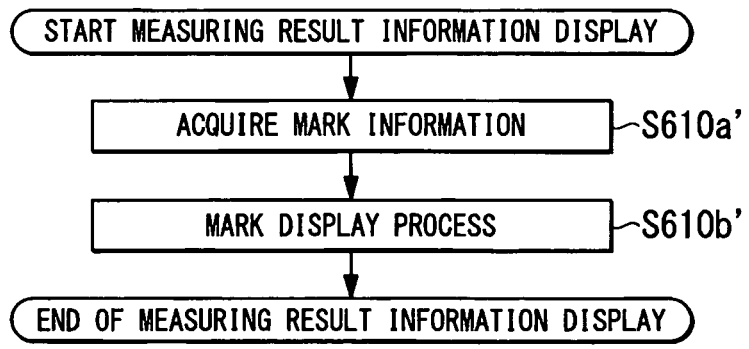
FIG. 35 is a flowchart illustrating procedures of the object measuring process (third operation example) according to another embodiment of the present invention.

FIG. 35 shows the details of step S610' in FIG. 33. The CPU 18 reads and acquires, from the RAM 14, the object distances at the points A1, A2 calculated in step S600c' in FIG. 34 and the spatial coordinates of the points A1, A2 on the object calculated in step S590' in FIG. 33 (step S610a'), and executes a display process for the mark for visualizing the size and inclination of the object (step S610b'). More specifically, the process of displaying the mark is executed in such a way as to provide a length (size) corresponding to the distance between the points A1, A2 on the display screen and a display mode to show the inclination of the object according to the object distances at the points A1, A2.

When the coordinates of the points A1, A2 on the display screen calculated in step S600c' in FIG. 34 lie outside the measurable area, it is not possible to display a mark in such a way that the mark is fitted in the measurable area. When coordinates of the points A1, A2 on the display screen are extremely close, a mark cannot be displayed in a visible manner. When one of the coordinates of the points A1, A2 on the display screen lie outside the measurable area, therefore, a value indicating the spatial distance is displayed like "- - -", whereas when coordinates of the points A1, A2 on the display screen are extremely close, a value indicating the spatial distance is displayed like "0.0 mm", so that both cases are handled as an error. In the above case, the mark may be displayed with a maximum or minimum size displayable.

According to the embodiment, as described above, the process of displaying a mark which indicates the size of the object and the inclination of the object in the depth direction of the image is executed, so that the size of the object and the inclination of the object in the depth direction of the image can be notified to the user in real time. This can increase the chance of acquiring necessary information without actually performing detailed measurement, thus ensuring the examination and observation efficiencies. Although the size of the object and the inclination of the object in the depth direction of the image are displayed by the same mark in the embodiment, a mark representing the size of the object and a mark representing the inclination of the object in the depth direction of the image may be displayed separately. Displaying the size of the object and the inclination of the object in the depth direction of the image are displayed by the same mark as done in the embodiment can permit a larger number of pieces of information to be displayed in smaller display space.

Further, it is possible to designate the size of a mark on the display screen with a point input (first and second operation examples) and designate the size of a mark on an object with a numerical input (third operation example), so that the examination effectively can be improved by the user's selecting a way of designating a mark according to the purpose of work.

In the first and second operation examples, the size of a mark on the display screen, once set, does not change, while the size of the mark on the object changes according to the object distance. In the third operation example, the size of a mark on the object input by the user does not change, while the size of the mark on the display screen changes according to the object distance.

In the mode where the size of a mark on the display screen changes as in the third operation example, the mark may not be fitted in the measurable area as the object distance becomes extremely short, or the mark may become too small as the object distance becomes extremely long. However, fixing the size of the mark on the display screen as in the first and second operation examples can make it easier to always compare the object with the mark. Because it is easier for the user to image the size of the object by comparing a mark with a predetermined length and predetermined size with the actual object, therefore, the size of the object can be made easier to see by fixing the size of the mark on the object as done in the third operation example.

Figure 37A:
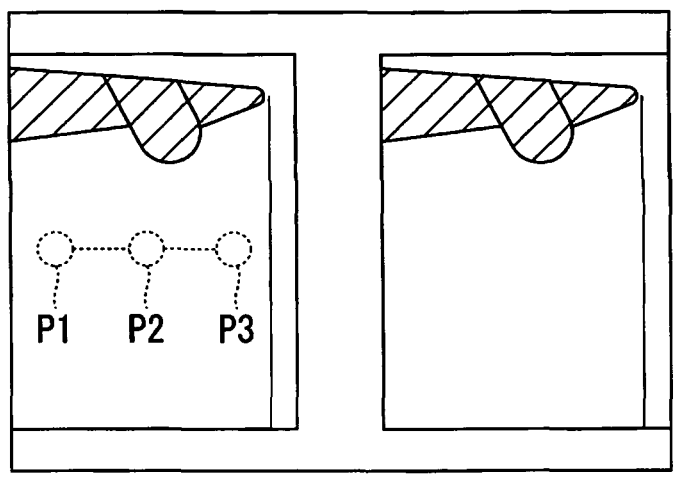
FIG. 37A is a reference diagram showing a display screen according to another embodiment of the present invention.
Figure 37B:
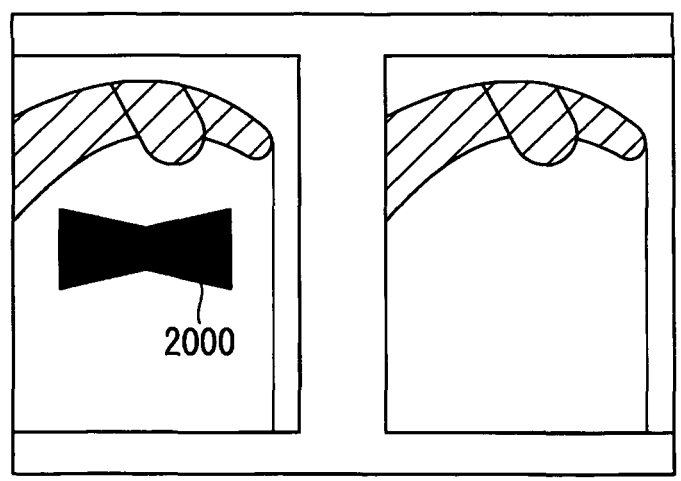
FIG. 37B is a reference diagram showing a display screen according to another embodiment of the present invention.

Although the detailed descriptions of the embodiments of the present invention have been given referring to the accompanying drawings, the specific configurations are not restricted to those of the embodiments and include design changes or the like without departing from the scope of the invention. For example, although the user input two points to be reference points for a mark in the first and second operation examples, the number of input points may be three or greater. FIG. 37A shows a display screen when the number of input points is three or greater. When the user designates points P1, P2, P3 as shown in FIG. 37A, a mark 2000 is displayed as shown in FIG. 37B.

In this case, the above-described processes are executed for the points P1, P2, and to the points P2, P3 to display a mark. The shape of the mark becomes a shape corresponding to the inclination of the object in the depth direction of the image, so that it is apparent that the object at the point P2 is located on the back side (far side) to the positions of the points P1, P3.

In addition, the inclination of the object in the depth direction of the image may be represented by the gray scale of a mark or a difference in color. When the object distance is far, for example, a mark may be displayed light, whereas when the object distance is near, the mark may be displayed dark. Alternatively, when the object distance is far, for example, a mark may be displayed in blue, whereas when the object distance is near, the mark may be displayed in red.

According to the present invention, the mark display section executes a process of displaying a first mark indicating the inclination of the object in the depth direction of the image, which brings about an effect of allowing a user to be notified of the inclination of the object in the depth direction of the image in real time. Further, according to the present invention, the mark display section executes a process of displaying a second mark indicating the size of the object, which brings about an effect of allowing a user to be notified of the size of the object together with the inclination of the object in the depth direction of the image in real time.

Although the foregoing description has been given of preferred embodiments of the present invention, the invention is not limited to those embodiments. It is possible to add, omit and replace structures and make other modifications without departing from the scope of the invention. The present invention is not to be limited to the details given herein, but may be limited only by the scope of the appended claims.

What is claimed is:

1. A measuring endoscope apparatus comprising:
an endoscope that photoelectrically converts an image of an object to generate an imaging signal,
a signal processing section that processes the imaging signal to generate image data,
a distance-measuring section that calculates object distances for a plurality of points on the object using the image data,
a display section that displays the image of the object based on the image data, and
a measuring section that determines a display appearance of a first mark to indicate an inclination of the object in a depthwise direction of the image based on the object distances for the plurality of points on the object, wherein the measuring section determines the display appearance of the first mark such that one portion of the first mark that corresponds to part of the object that is closer is larger than another portion of the first mark that corresponds to part of the object that is farther away,
wherein the display section displays the first mark.

2. The measuring endoscope apparatus according to claim 1, wherein the measuring section calculates a size of another mark that indicates a size of the object based on another object distance and a view angle of the endoscope.

3. The measuring endoscope apparatus according to claim 2, wherein the measuring section calculates a size of the another mark on the object at a position apart by the another object distance based on the another object distance, the view angle of the endoscope and a display size of the another mark.

4. The measuring endoscope apparatus according to claim 2, wherein the measuring section calculates a display size of the another mark based on the another object distance, the view angle of the endoscope and a size of the another mark on the object at a position apart by the another object distance.

5. The measuring endoscope apparatus according to claim 2, wherein the display section displays the image of the object and displays the another mark overlying an aim indicating an object distance measuring point of the another object distance.

6. The measuring endoscope apparatus according to claim 2, wherein the display section displays the image of the object and the another mark and displays a value of a size of the another mark on the object at a position apart by the another object distance.

7. The measuring endoscope apparatus according to claim 2, wherein the display section displays the image of the object and displays the another mark around a frame of the image of the object.

8. The measuring endoscope apparatus according to claim 2, wherein the display section displays the image of the object and the another mark and displays the another object distance.

9. The measuring endoscope apparatus according to claim 1, wherein the measuring section further calculates distances among the plurality of points on the object based on spatial coordinates of the plurality of points, and calculates a size of a second mark that indicates a size of the object and a distance between two points on the object based on positions of a plurality of points on an image forming surface of the endoscope corresponding to the plurality of points on the object.

10. The measuring endoscope apparatus according to claim 9, wherein the first mark and the second mark are identical.

11. The measuring endoscope apparatus according to claim 1, wherein the measuring section further calculates distances among the plurality of points on the object based on spatial coordinates of the plurality of points on the object, and calculates a size of a second mark that indicates a size of the object based on a preset numerical value indicating a distance on the object and the distances among the plurality of points on the object calculated by the measuring section.

12. The measuring endoscope apparatus according to claim 11, wherein the display section further displays the distances among the plurality of points on the object.

13. The measuring endoscope apparatus according to claim 12, wherein the display section displays the distances among the plurality of points on the object over the image of the object.

14. The measuring endoscope apparatus according to claim 12, wherein the display section displays the distances among the plurality of points on the object at a location other than where the image of the object is displayed.

15. The measuring endoscope apparatus according to claim 12, wherein the display section displays the distances among the plurality of points on the object in a vicinity of the second mark.

16. The measuring endoscope apparatus according to claim 1, wherein the distance measuring section calculates spatial coordinates of the plurality of points on the object and calculates object distances to an image forming surface of the endoscope from the points on the object using the image data.

* * * * *